United States Patent
Liu et al.

(10) Patent No.: US 11,091,485 B2
(45) Date of Patent: Aug. 17, 2021

(54) IMIDAZO[1',2':1,6]PYRIDO[2,3-D]PYRIMIDINE COMPOUND AS PROTEIN KINASE INHIBITOR

(71) Applicant: SHENGKE PHARMACEUTICALS (JIANGSU) LTD., Jiangsu (CN)

(72) Inventors: Bin Liu, San Diego, CA (US); Hang Cheng, Sichuan (CN); Weiyan Xiong, Sichuan (CN); Chenggang Zhang, Jiangsu (CN); Chengzhi Yu, San Diego, CA (US)

(73) Assignee: SHENGKE PHARMACEUTICALS (JIANGSU) LTD., Suzhou (CN)

( * ) Notice: Subject to any disclaimer, the term of this patent is extended or adjusted under 35 U.S.C. 154(b) by 0 days.

(21) Appl. No.: 16/619,222

(22) PCT Filed: May 21, 2018

(86) PCT No.: PCT/CN2018/087665
§ 371 (c)(1),
(2) Date: Dec. 4, 2019

(87) PCT Pub. No.: WO2018/214846
PCT Pub. Date: Nov. 29, 2018

(65) Prior Publication Data
US 2020/0270251 A1    Aug. 27, 2020

(30) Foreign Application Priority Data

May 23, 2017 (CN) .......................... 201710368799.3

(51) Int. Cl.
*C07D 471/14*    (2006.01)
*C07D 519/00*    (2006.01)

(52) U.S. Cl.
CPC ......... *C07D 471/14* (2013.01); *C07D 519/00* (2013.01)

(58) Field of Classification Search
CPC .................................................. C07D 471/14
See application file for complete search history.

(56) References Cited

FOREIGN PATENT DOCUMENTS

| | | |
|---|---|---|
| CN | 105481858 A | 4/2016 |
| WO | 2003/082871 A1 | 10/2003 |
| WO | 2013/007708 A1 | 1/2013 |

OTHER PUBLICATIONS

Stella (J. Pharmaceutical Sciences, 2010, 99(12), pp. 4755-4765).*
International Search Report and Written Opinion for Application No. PCT/CN2018/087665, dated Jul. 4, 2018, 8 pages.

* cited by examiner

*Primary Examiner* — Susanna Moore
(74) *Attorney, Agent, or Firm* — McCarter & English, LLP; Xin Zhang

(57) ABSTRACT

Provided is an imidazo[1',2':1,6]pyrido[2,3-d]pyrimidine compound of general formula (I). The compound can be used in treating a cell proliferative disorder and is a cyclin-dependent kinase (CDK) inhibitor with broad-spectrum and strong activity.

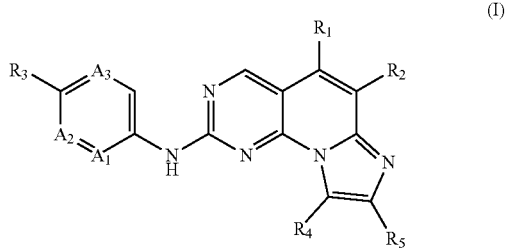

18 Claims, No Drawings

IMIDAZO[1',2':1,6]PYRIDO[2,3-D]PYRIMIDINE COMPOUND AS PROTEIN KINASE INHIBITOR

CROSS-REFERENCE TO RELATED APPLICATIONS

The present application is a national stage entry of PCT/CN2018/087665 filed on May 21, 2018, which claims the priority of the Chinese Patent Application No. 201710368799.3 filed on May 23, 2017. The entire contents of the aforementioned applications are incorporated herein by reference.

FIELD OF THE INVENTION

The present disclosure provides a class of imidazo[1',2':1,6]pyrido[2,3-d]pyrimidine compounds as inhibitors of cyclin-dependent kinase (CDK), which have a broad-spectrum and strong inhibitory activity against CDK, The compounds of the present disclosure are effective in treating diseases such as cancer, inflammation, etc.

BACKGROUND OF THE INVENTION

Cancer is the second leading cause of death globally, According to the 'Global Cancer Report 2014' published by World Health Organization, the number of cancer patients and deaths worldwide is increasing alarmingly. Nearly half of the new cancer cases are in Asia, and most of them are in China. The report also predicts that the number of cancer cases worldwide will increase rapidly, from 14 million in 2012 to 19 million in 2025, and to 24 million by 2035, of which China will account for 21.9%. According to institutional data, in the past 30 years, cancer mortality rate in China has increased by 80%, and about 2.6 million cancer cases and 1.8 million deaths occur annually.

Cell cycle is an important part of cellular activities. Studies have shown that tumorigenesis and progression of many malignancies are closely related to the disorder of cell cycle regulation mechanism, so that tumors are considered as a kind of disease relating to cell cycle. Since the 1970s, three scientists from the United States and UK have successively discovered the important roles of cyclin-dependent kinase and cyclin in cell regulation, thus winning the 2001 Nobel Prize in Physiology/Medicine. With the great progress in the study of cell cycle regulation mechanism, especially the discovery of the core role of CDK in cell cycle regulation, cyclin-dependent kinase has become a hotspot of anticancer drug research in recent years. At present, CDK1, 2, 4, 6 and 7 are considered to be the major regulators of cell cycle.

In addition to the selective inhibitors of CDK4 and 6, pan-CDK inhibitors such as Dinaciclib (SCH-727965, MK-7965), which have inhibitory activities against CDK1, CDK2, CDK5, CDK9 and CDK12, have entered the stage of clinical trials, showing promising anticancer activities in targeted therapy for solid tumors.

More CDK inhibitors are needed to meet the clinical needs of various diseases, CDK inhibitors with higher effectiveness and selective activity show better therapeutic benefits for specific diseases (such as cancer, cardiovascular disorders, infectious diseases, autoimmune diseases, etc.) and therefore become the goal has been pursuing in the field.

SUMMARY OF THE INVENTION

The present disclosure provides a class of imidazo[1',2':1,6]pyrido[2,3-d]pyrimidine compounds as inhibitors of cyclin-dependent kinase, which have a broad-spectrum and strong inhibitory activity. The compounds of the present disclosure are effective in treating cell proliferative diseases, such as restenosis, cancer and inflammation. Compared with the existing drugs, the compounds of the present disclosure can further improve the pharmacokinetic properties, including the significant improvement in the metabolic stability and clearance rate over the existing compounds. Furthermore, the compounds of the present disclosure can be readily synthesized and can be administered to the patients by a variety of methods.

In one aspect, the present disclosure provides a compound of general formula (I), or pharmaceutically acceptable salts, enantiomers, diastereomers, racemates, solvates, hydrates, polymorphs, prodrugs or isotope variants thereof, and mixtures thereof:

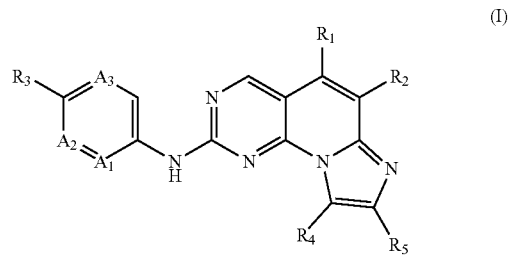

(I)

wherein:
$A_1$ is selected from $CR_3$ or N;
$A_2$ is selected from $CR_3$;
$A_3$ is selected from $CR_3$;
$R_1$ is hydrogen;
$R_2$ is selected from hydrogen, halogen, —CN, —$OR_a$, —$SR_a$, —$NR_bR_c$, —$C(O)R_a$, —$C(O)OR_a$, —$C(O)NR_bR_c$, $C_{1-6}$alkyl or $C_{1-6}$haloalkyl;
$R_3$ is selected from hydrogen, halogen, —CN, —$NO_2$, —$OR_a$, —$SR_a$, —$NR_bR_c$, —O—$C_{1-6}$ alkylene-$R_6$, $C_{1-6}$ alkyl, $C_{1-6}$haloalkyl, -L'-$C_{3-7}$cycloalkyl, -L'-3- to 11-membered heterocyclyl, -L'-$C_{6-10}$ aryl or -L'-5- to 10-membered heteroaryl, said groups are optionally substituted with 1, 2, 3, 4 or 5 $R_6$ groups;
$R_4$ is selected from hydrogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
$R_5$ is hydrogen;
$R_6$ is selected from hydrogen, —$NH_2$, —$NHC_{1-6}$alkyl, —$N(C_{1-6}$alkyl$)_2$, $C_{1-6}$alkyl or $C_{1-6}$haloalkyl;
or two $R_6$ groups on a same carbon atom are taken together to form oxo or thioxo;
wherein:
$R_4$ is optionally substituted with 1, 2 or 3 R' groups, wherein R' is independently selected from hydrogen, halogen, —CN, —$NO_2$, —$OR_a$, —$SR_a$, —$NR_bR_c$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
$R_a$ is independently selected from hydrogen, $C_{1-6}$ alkyl, $C_{2-6}$ alkenyl, $C_{2-6}$ alkynyl or $C_{1-6}$ haloalkyl;
$R_b$ and $R_c$ are independently selected from hydrogen, $C_{1-6}$ alkyl, $C_{2-6}$ alkenyl, $C_{2-6}$ alkynyl or $C_{1-6}$ haloalkyl; or $R_b$, $R_c$ and N atom are taken together to form a 3- to 7-membered heterocyclyl;
L' is selected from a chemical bond or —O—.

In another aspect, the present disclosure provides a pharmaceutical composition comprising a compound of the present disclosure, and optionally pharmaceutically acceptable excipients.

In another aspect, the present disclosure provides a pharmaceutical composition comprising a compound of the present disclosure and pharmaceutically acceptable excipients, which also includes other therapeutic agents.

In another aspect, the present disclosure provides a kit comprising a compound of the present disclosure, other therapeutic agents and pharmaceutically acceptable carriers, adjuvants or vehicles.

In another aspect, the present disclosure provides use of a compound of the present disclosure in the preparation of a medicament for the treatment and/or prevention of CDK-mediated diseases.

In another aspect, the present disclosure provides a method of treating and/or preventing CDK-mediated diseases in a subject, including administering a compound of the present disclosure or a composition of the present disclosure to the subject.

In another aspect, the present disclosure provides a compound or a composition of the present disclosure, for use in treating and/or preventing CDK-mediated diseases.

In a specific embodiment, the diseases described herein include cell proliferative diseases, which include but are not limited to cancers, cardiovascular disorders, infectious diseases, chronic inflammatory diseases, autoimmune disorders and other cell proliferative disorders. More specifically, the cancers described herein include, but are not limited to, solid tumors and hematological malignancies, such as breast cancer, neuroblastoma, malignant rhabdomyoma, well-differentiated and dedifferentiated liposarcoma, glioma, lung cancer, colorectal cancer, gastric cancer, gastrointestinal stromal tumors (GIST), hepatocellular carcinoma, prostatic tumors, sarcoma, ovarian cancer, cervical cancer, pancreatic cancer, melanoma, thyroid cancer, carcinoma of bite duct, endometrial cancer, renal cancer, mesothelioma, lymphoma, leukemia, non-Hodgkin's lymphoma, mantle cell lymphoma, anaplastic large cell lymphoma, acute myeloid leukemia (AML), and multiple myeloma. The cardiovascular disorders described herein include restenosis, atherosclerosis, vascular smooth muscle proliferation and intimal hyperplasia secondary to balloon angioplasty, and other vascular disorders caused by abnormal cell proliferation. The infectious diseases described herein include infections of fungi, protozoan parasites (such as *Plasmodium falciparum*) and DNA and RNA virus, such as herpes simplex virus (HSV) infections. The chronic inflammatory diseases described herein are such as rheumatoid arthritis. Other cell proliferative disorders described herein include psoriasis (characterized by excessive proliferation of keratinocytes), glomerulonephritis and lupus.

Other objects and advantages of the present disclosure will be apparent to those skilled in the art from the subsequent specific embodiments, examples and claims.

Definitions

Chemical Definitions

Definitions of specific functional groups and chemical terms are described in more detail hereafter.

When a range of values is listed, each value and sub-range within the range are intended to be included. For example, "$C_{1-6}$alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight or branched, saturated hydrocarbon group having 1 to 6 carbon atoms. In some embodiments, $C_{1-4}$ alkyl is preferred. Examples of $C_{1-6}$ alkyl include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentyl ($C_5$), pentyl ($C_5$), neopentyl ($C_5$), 3-methyl-2-butyl ($C_5$), tert-pentyl ($C_5$) and n-hexyl ($C_6$). The term "$C_{1-6}$ alkyl" also includes heteroalkyl, wherein one or more (e.g., 1, 2, 3 or 4) carbon atoms are substituted with heteroatoms (e.g., oxygen, sulfur, nitrogen, boron, silicon, phosphorus). Alkyl groups can be optionally substituted with one or more substituents, for example, with 1 to 5 substituents, 1 to 3 substituents or 1 substituent. Conventional abbreviations of alkyl include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$) or i-Bu (—$CH_2CH(CH_3)_2$).

"$C_{2-6}$ alkenyl" refers to a radical of a straight or branched hydrocarbon group having 2 to 6 carbon atoms and at least one carbon-carbon double bond. In some embodiments, $C_{2-4}$ alkenyl is preferred. Examples of $C_{2-6}$ alkenyl include vinyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), etc. The term "$C_{2-6}$ alkenyl" also includes heteroalkenyl, wherein one or more (e.g., 1, 2, 3 or 4) carbon atoms are replaced by heteroatoms (e.g., oxygen, sulfur, nitrogen, boron, silicon, phosphorus). The alkenyl groups can be optionally substituted with one or more substituents, for example, with 1 to 5 substituents, 1 to 3 substituents or 1 substituent.

"$C_{2-6}$ alkynyl" refers to a radical of a straight or branched hydrocarbon group having 2 to 6 carbon atoms, at least one carbon-carbon triple bond and optionally one or more carbon-carbon double bonds. In some embodiments, $C_{2-4}$ alkynyl is preferred. Examples of $C_{2-6}$ alkynyl include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), etc. The term "$C_{2-6}$ alkynyl" also includes heteroalkynyl, wherein one or more (e.g., 1, 2, 3 or 4) carbon atoms are replaced by heteroatoms (e.g., oxygen, sulfur, nitrogen, boron, silicon, phosphorus). The alkynyl groups can be substituted with one or more substituents, for example, with 1 to 5 substituents, 1 to 3 substituents or 1 substituent.

"$C_{1-6}$ alkylene" refers to a divalent group formed by removing another hydrogen of the $C_{1-6}$ alkyl, and can be a substituted or unsubstituted alkylene. In some embodiments, $C_{1-4}$ alkylene is particularly preferred. The unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), etc. Examples of substituted alkylene groups, such as those substituted with one or more alkyl (methyl) groups, include, but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), etc.

"Halo" or "halogen" refers to fluorine (F), chlorine (Cl), bromine (Br) and iodine (I).

"$C_{1-6}$ haloalkyl" represents the "$C_{1-6}$ alkyl" described above, which is substituted with one or more halogen groups, Examples include the mono-, di-, poly-halogenated, including perhalogenated, alkyl. A monohalogen substituent may have one iodine, bromine, chlorine or fluorine atom in the group; a dihalogen substituent and a polyhalogen substituent may have two or more identical halogen atoms or a combination of different halogens. Examples of preferred haloalkyl groups include monofluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The haloalkyl groups can be substituted at any available point of attachment, for example, with 1 to 5 substituents, 1 to 3 substituents or 1 substituent.

"$C_{3-7}$ cycloalkyl" refers to a radical of non-aromatic cyclic hydrocarbon group having 3 to 7 ring carbon atoms and zero heteroatoms, in some embodiments, $C_{3-6}$ cycloalkyl is particularly preferred, and $C_{5-6}$ cycloalkyl is more preferred. The cycloalkyl also includes a ring system in which the cycloalkyl described herein is fused with one or more aryl or heteroaryl groups, wherein the point of attachment is on the cycloalkyl ring, and in such case, the number of carbon atoms continues to represent the number of carbon atoms in the cycloalkyl system. Exemplary cycloalkyl groups include, but are not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), etc.

"3- to 11-membered heterocyclyl" refers to a radical of 3- to 11-membered non-aromatic ring system having ring carbon atoms and 1 to 5 ring heteroatoms, wherein each of the heteroatoms is independently selected from nitrogen, oxygen, sulfur, boron, phosphorus and silicon. In the heterocyclyl containing one or more nitrogen atoms, the point of attachment can be a carbon or nitrogen atom as long as the valence permits. In some embodiments, 3- to 9-membered heterocyclyl is preferred, which is a radical of 3- to 9-membered non-aromatic ring system having ring carbon atoms and 1 to 5 ring heteroatoms. In some embodiments, 3- to 7-membered heterocyclyl is preferred, which is a radical of 3- to 7-membered non-aromatic ring system having ring carbon atoms and 1 to 4 ring heteroatoms. 3- to 6-membered heterocyclyl is preferred, which is a radical of 3- to 6-membered non-aromatic ring system having ring carbon atoms and 1 to 3 ring heteroatoms. 4- to 6-membered heterocyclyl is preferred, which is a radical of 4- to 6-membered non-aromatic ring system having ring carbon atoms and 1 to 3 ring heteroatoms. 5- to 6-membered heterocyclyl is more preferred, which is a radical of 5- to 6-membered non-aromatic ring system having ring carbon atoms and 1 to 3 ring heteroatoms. The heterocyclyl also includes a ring system wherein the heterocyclyl described above is fused with one or more cycloalkyl groups, wherein the point of attachment is on the cycloalkyl ring, or the heterocyclyl described above is fused with one or more aryl or heteroaryl groups, wherein the point of attachment is on the heterocyclyl ring; and in such cases, the number of ring members continues to represent the number of ring members in the heterocyclyl ring system. Exemplary 3-membered heterocyclyl groups containing one heteroatom include, but are not limited to, aziridinyl, oxiranyl and thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydroniranyl, dihydrofuranyl, tetrahydrothiophenyl, dihydrothienyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl, and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidyl, tetrahydropyranyl, dihydropyridyl and thianyl. Exemplary 6-membered heterocyclyl groups containing two heteroatoms include, but are not limited to, piperazinyl, morpholinyl, dithianyl and dioxanyl. Exemplary 6-membered heterocyclyl groups containing three heteroatoms include, but are not limited to, triazinanyl. Exemplary 7-membered heterocycyl groups containing one heteroatom include, but are not limited to, azepanyl, oxepanyl and thiepanyl. Exemplary 5-membered heterocyclyl groups fused with a $C_6$ aryl (also referred as 5,6-bicyclic heterocyclyl herein) include, but are not limited to, indolinyl, isoindolinyl, dihydrobenzofuranyl, dihydrobenzothiophenyl, benzoxazolinonyl, etc. Exemplary 6-membered heterocyclyl groups fused with a $C_6$ aryl (also referred as 6,6-bicyclic heterocyclyl herein) include, but are not limited to, tetrahydroquinolinyl, tetrahydroisoquinolinyl, etc.

The 3- to 11-membered heterocyclyl also includes spiroheterocyclyl, that is, a group in which two rings (e.g., a heterocycle and a carbocycle) share a carbon atom, wherein at least one of the rings is a heterocyclyl as defined above. More specifically, the spiroheterocyclyl is a spiro ring formed by two 4-membered rings, two 5-membered rings, two 6-membered rings, one 4-membered ring and one 5-membered ring, one 4-membered ring and one 6-membered ring, or one 5-membered ring and one 6-membered ring, wherein at least one of the rings is a 4- to 6-membered heterocyclyl as defined above. The 4- to 6-membered heterocyclyl containing 1, 2 or 3 O, N or S heteroatoms is preferred. The 4- to 6-membered heterocyclyl containing 1 N heteroatom is more preferred: Specific spiroheterocyclyl groups include, but are not limited to:

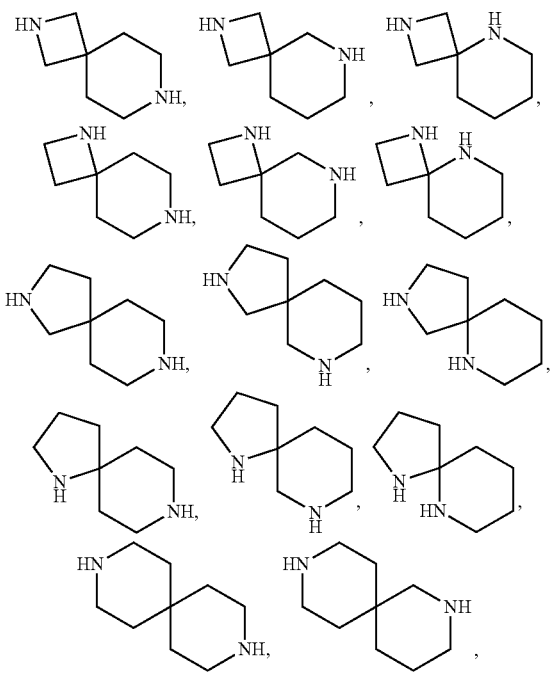

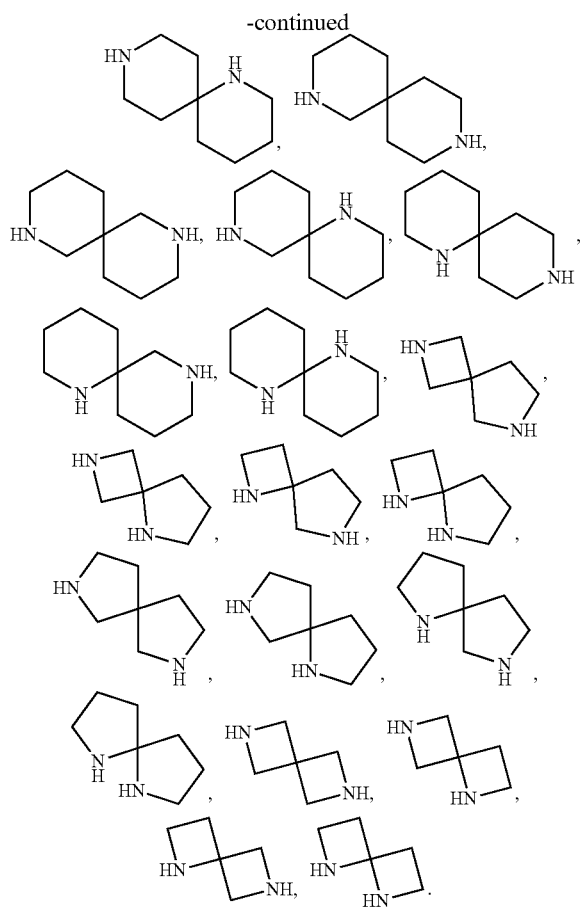

Specific examples of preferred heterocyclyl groups include, pyrrolinyl, imidazolidinyl, pyrazolidinyl, tetrahydropyranyl, dihydropyranyl, dihydrofuranyl, thiazolidinyl, dihydrothiazolyl, 2,3-dihydro-benzo[1,4]dioxol, indolinyl, isoindolinyl, dihydrobenzothiophene, dihydrobenzofuranyl, isodihydrobenzopyranyl, dihydrobenzopyranyl, 1,2-dihydroisoquinoline 1,2,3,4-tetrahydroisoquinoline, 1,2,3,4-tetrahydroquinoline, 2,3,4,4a,9,9a-hexahydro-1H-3-azafluorene, 5,6,7-trihydro-1,2,4-triazolo[3,4-a]isoquinolyl, 3,4-dihydro-2H-benzo[1,4]oxazinyl, benzo[1,4]dioxol, 2,3-dihydro-1H-1k'-benzo[d]isothiazol-6-yl, 2,3-di-benzo[1,4] dioxinyl, dihydrobenzofuran, 2-oxoaziridin-1-yl, 2-oxoazetidin-1-yl, 2-oxopyrrolidin-1-yl, 2-oxopiperidin-1-yl, 2-oxoazepan-1-yl, 2-oxoazocan-1-yl, 2-oxoazonan-1-yl, 2-oxoazecan-1-yl, aziridine, azetidine, pyrrolidinyl, piperidine, azepane, azocane, azocane, azocane, piperidyl, piperazinyl, morpholinyl, diazaspiro[3,3]heptane, diazaspiro[3,4] octane, diazaspiro[3,5]nonane, diazaspiro[4,4]nonane, diazaspiro[4,5]decane and diazaspiro[5,5]undecane.

"$C_{6-10}$ aryl" refers to a radical of monocyclic or polycyclic (e.g., bicyclic) 4n+2 aromatic ring system having 6-10 ring carbon atoms and zero heteroatoms (e.g., having 6 or 10 shared a electrons in a cyclic array). In some embodiments, the aryl group has six ring carbon atoms ("$C_6$ aryl"; for example, phenyl). In some embodiments, the aryl group has ten ring carbon atoms ("$C_{10}$ aryl"; for example, naphthyl, e.g., 1-naphthyl and 2-naphthyl). The aryl group also includes a ring system in which the aryl ring described above is fused with one or more cycloalkyl or heterocyclyl groups, and the point of attachment is on the aryl ring, in which case the number of carbon atoms continues to represent the number of carbon atoms in the aryl ring system.

"5- to 10-membered heteroaryl" refers to a radical of 5- to 10-membered monocyclic or bicyclic 4n+2 aromatic ring system (e.g., having 6 or 10 shared π electrons in a cyclic array) having ring carbon atoms and 1-4 ring heteroatoms, wherein each heteroatom is independently selected from nitrogen, oxygen and sulfur. In the heteroaryl group containing one or more nitrogen atoms, the point of attachment can be a carbon or nitrogen atom as long as the valence permits. Heteroaryl bicyclic systems may include one or more heteroatoms in one or two rings. Heteroaryl also includes ring systems wherein the heteroaryl ring described above is fused with one or more cycloalkyl or heterocyclyl groups, and the point of attachment is on the heteroaryl ring. In such case, the number the carbon atoms continues to represent the number of carbon atoms in the heteroaryl ring system. In some embodiments, 5- to 6-membered heteroaryl groups are particularly preferred, which are radicals of 5- to 6-membered monocyclic or bicyclic 4n+2 aromatic ring systems having ring carbon atoms and 1-4 ring heteroatoms. Exemplary 5-membered heteroaryl groups containing one heteroatom include, but are not limited to, pyrrolyl, furyl and thienyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl, and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzoisoxazolyl, benzoxadiazolyl, benzothiazolyl, benzoisothiazolyl, benzothiadiazolyl, indolizinyl and purinyl. Exemplary 6,6-bicyclic heteroaryl groups include, but are not limited to, naphthyridinyl, pteridinyl, quinolyl, isoquinolyl, cinnolinyl, quinoxalinyl, phthalazinyl and quinazolinyl.

Specific examples of preferred heteroaryl groups include: pyrrolyl, imidazolyl, pyrazolyl, 2-pyridyl, 3-pyridyl, 4-pyridyl, pyrimidinyl, pyrazinyl, pyridazinyl, triazolyl (4H-1,2,4-triazolyl, 1H-1,2,3-triazolyl, 2H-1,2,3-triazolyl, pyranyl, 2-furyl, 3-furyl, 2-thienyl, 3-thienyl, oxazolyl, isoxazolyl, oxazolyl (1,2,4-oxazolyl, 1,3,4-oxazolyl, 1,2,5-oxazolyl, thiazolyl, thiadiazolyl (1,2,4-thiadiazolyl, 1,3,4-thiadiazolyl, 1,2,5-thiadiazolyl).

"Oxo" represents =O.
"Thioxo" represents =S.

Alkyl, alkenyl, alkynyl, carbocyclyl, heterocyclyl, aryl and heteroaryl as defined herein are optionally substituted groups.

Exemplary substituents on carbon atoms include, but are not limited to, halogen, —CN, —NO$_2$, —N$_3$, —SO$_2$H, —SO$_3$H, —OH, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$), —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), alkyl, haloalkyl, alkenyl, alkynyl, carbocyclyl, heterocyclyl, aryl and heteroaryl, wherein each of the alkyl, alkenyl, alkynyl, carbocyclyl, heterocyclyl, aryl and heteroaryl is independently substituted with 0, 1, 2, 3, 4 or 5 R$^{dd}$ groups;

or two geminal hydrogen on a carbon atom are replaced with =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$ or =NOR$^{cc}$ groups;

each of the R$^{aa}$ is independently selected from alkyl, haloalkyl, alkenyl, alkynyl, carbocyclyl, heterocyclyl, aryl and heteroaryl, or two of the R$^{aa}$ groups are combined to form a heterocyclyl or heteroaryl ring, wherein each of the alkyl, alkenyl, alkynyl, carbocyclyl, heterocyclyl, aryl and heteroaryl is independently substituted with 0, 1, 2, 3, 4 or 5 R$_{dd}$ groups;

each of the R$^{bb}$ is independently selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_3$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl and heteroaryl, or two R$^{bb}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups;

each of the R$^{cc}$ is independently selected from hydrogen, alkyl, haloalkyl, alkenyl, alkynyl, carbocyclyl, heterocyclyl, aryl and heteroaryl, or two R$^{cc}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$_{dd}$ groups;

each of the R$^{dd}$ is independently selected from halogen, —CN, —NO$_2$, —N$_3$; —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$), —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, alkyl, haloalkyl, alkenyl, alkynyl; carbocyclyl, heterocyclyl, aryl and heteroaryl, wherein each of the alkyl, alkenyl, alkynyl, carbocyclyl, heterocyclyl, aryl and heteroaryl is independently substituted with 0, 1, 2, 3, 4 or 5 R$^{gg}$ groups, or two geminal R$^{dd}$ substituents can be combined to form =O or =S;

each of the R$^{ee}$ is independently selected from alkyl, haloalkyl, alkenyl, alkynyl, carbocyclyl, aryl, heterocyclyl, and heteroaryl, wherein each of the alkyl, alkenyl, alkynyl, carbocyclyl, heterocyclyl, aryl and heteroaryl is independently substituted with 0, 1, 2, 3, 4 or 5 R$^{gg}$ groups;

each of the R$^{ff}$ is independently selected from hydrogen, alkyl, haloalkyl, alkenyl, carbocyclyl, heterocyclyl, aryl and heteroaryl, or two R$^{ff}$ groups are combined to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{gg}$ groups;

each of the R$^{gg}$ is independently selected from halogen, —CN, —NO$_2$, —N$_3$, —SO$_2$H, —SO$_3$H, —OH, —OC$_{1-6}$alkyl, —ON(C$_{1-6}$alkyl), —N(C$_{1-6}$alkyl)$_2$, —N(C$_{1-6}$alkyl)$_3$$^+$X$^-$, —NH(C$_{1-6}$alkyl)$^+$X$^-$, —NH$_2$(C$_{1-6}$alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$, —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ haloalkyl, C$_2$-C$_6$ alkenyl, C$_2$-C$_6$ alkynyl, C$_3$-C$_7$ carbocyclyl, C$_6$-C$_{10}$ aryl, C$_3$-C$_7$ heterocyclyl, C$_5$-C$_{10}$ heteroaryl; or two geminal R$^{gg}$ substituents may combine to form =O or =S; wherein X$^-$ is a counter-ion.

Exemplary substituents on nitrogen atoms include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, alkyl, haloalkyl, alkenyl, alkynyl, carbocyclyl, heterocyclyl, aryl and heteroaryl, or two R$^{cc}$ groups attached to a nitrogen atom combine to form a heterocyclyl or a heteroaryl ring, wherein each of the alkyl, alkenyl, alkynyl, carbocyclyl, heterocyclyl, aryl and heteroaryl is independently substituted with 0, 1, 2, 3, 4 or 5 R$^{dd}$ groups, and wherein R$^{aa}$, R$^{bb}$, R$^{cc}$ and R$^{dd}$ are as described herein.

Other Definitions

The term "cancer" includes, but is not limited to, the following cancers: breast, ovary, cervix, prostate, testis, esophagus, stomach, skin, lung, bone, colon, pancreas, thyroid, biliary tract, buccal cavity and pharynx (mouth), lips, tongue, oral cavity, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, liver cancer, kidney cancer, bone marrow disorder, lymphatic disorder, Hodgkin's disease, hairy cell carcinoma and leukemia.

The term "treating" as used herein relates to reversing, alleviating or inhibiting the progression or prevention of the disorders or conditions to which the term applies, or of one or more symptoms of such disorders or conditions. The noun "treatment" as used herein relates to the action of treating, which is a verb, and the latter is as just defined.

The term "pharmaceutically acceptable salt" as used herein refers to those carboxylate and amino acid addition salts of the compounds of the present disclosure, which are suitable for the contact with patients' tissues within a reliable medical judgment, and do not produce inappropriate toxicity, irritation, allergy, etc. They are commensurate with a reasonable benefit/risk ratio, and are effective for their intended use. The term includes, if possible, the zwitterionic form of the compounds of the disclosure.

The term "salt" refers to a relatively non-toxic addition salt of inorganic and organic acids to the compounds of the present disclosure. These salts can be prepared in situ during the final separation and purification of the compounds, or by isolating salts produced by separately reacting the purified compound in the free base form with a suitable organic or inorganic acid. As long as the compounds of the present disclosure are basic compounds, they are capable of forming a plurality of different salts with various inorganic and organic acids. Although such salts must be pharmaceutically acceptable for animal administration, it is often necessary in practice that the pharmaceutically unacceptable salts of the basic compounds are first isolated from the reaction mixture, and then they are simply treated with an alkaline agent to convert to the free base compound, followed by the conversion of the free base to pharmaceutically acceptable acid addition salts. The acid addition salts of the basic compounds are prepared by contacting the free base form with a sufficient amount of the acid required in a conventional manner to form the salts. The free base can be regenerated by contacting the salt form with the base in a conventional manner and then isolating the free base. The free base forms are somewhat different from their respective salt forms in some physical properties, such as solubility in polar solvents. But for the purposes of the present disclosure, the salts are still equivalent to their respective free bases.

The pharmaceutically acceptable base addition salts are formed with metals or amines, such as alkali metal and alkaline earth metal hydroxides or organic amines. Examples of the metals used as cations include sodium, potassium, magnesium, calcium, etc. Examples of suitable amines are N,N'-dibenzylethylenediamine, chloroprocaine, choline, diethanolamine, ethylenediamine, N-methylglucamine and procaine.

The base addition salt of the acidic compound can be prepared by contacting the free acid form with a sufficient amount of the required base to form a salt in a conventional manner. The free acid can be regenerated by contacting the salt form with an acid in a conventional manner and then isolating the free acid. The free acid forms are somewhat different from their respective salt forms in their physical properties, such as solubility in polar solvents. But for the purposes of the present disclosure, the salts are still equivalent to their respective free acids.

The salts can be prepared from the inorganic acids, which include sulfates, pyrosulfates, bisulfates, sulfites, bisulfites, nitrates, phosphates, monohydrogen phosphates, dihydrogen phosphates, metaphosphates, pyrophosphates, chlorides, bromides and iodides, Examples of the acids include hydrochloric acid, nitric acid, sulfuric acid, hydrobromic acid, hydroiodic acid, phosphoric acid, etc. The representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthalate, methanesulfonate, glucoheptanate, lactobionate, lauryl sulfonate, isethionate, etc. The salts can also be prepared from the organic acids, which include aliphatic monocarboxylic and dicarboxylic acids, phenyl-substituted alkanoic acids, hydroxyalkanoic acids, alkanedioic acid, aromatic acids, aliphatic and aromatic sulfonic acids, etc. The representative salts include acetate, propionate, octanoate, isobutyrate, oxalate, malonate, succinate, suberate, sebacate, fumarate, maleate, mandelate, benzoate, chlorobenzoate, methyl benzoate, dinitrobenzoate, naphthoate, besylate, tosylate, phenylacetate, citrate, lactate, maleate, tartrate, methanesulfonate, etc. The pharmaceutically acceptable salts can include cations based on alkali metals and alkaline earth metals, such as sodium, lithium, potassium, calcium, magnesium, etc., as well as non-toxic ammonium, quaternary ammonium, and amine cations including, but not limited to, ammonium, tetramethylammonium, tetraethylammonium, methylamine, dimethylamine, trimethylamine, triethylamine, ethylamine, etc. Salts of amino acids are also included, such as arginine salts, gluconates, galacturonates, etc. (for example, see Berge S. M. et al., "Pharmaceutical Salts," J. Pharm. Sci., 1977; 66: 1-19 for reference).

Examples of pharmaceutically acceptable non-toxic amides of the compounds of the disclosure include $C_1$-$C_6$ alkyl esters, wherein the alkyl group is straight or branched. Acceptable esters also include $C_5$-$C_7$ cycloalkyl esters as well as arylalkyl esters, such as, but not limited to, benzyl esters. $C_1$-$C_4$ alkyl esters are preferred. Esters of the compounds of the disclosure can be prepared according to the conventional methods, for example, March's Advanced Organic Chemistry, 5 Edition, M. B. Smith & J. March, John Wiley & Sons, 2001.

Examples of pharmaceutically acceptable non-toxic amides of the compounds of the disclosure include amides derived from ammonia, primary $C_1$-$C_6$ alkylamines and secondary $C_1$-$C_6$ dialkylamines, wherein the alkyl group is straight or branched. In the case of the secondary amine, the amine may also be in the form of a 5- or 6-membered heterocycle containing one nitrogen atom. Amides derived from ammonia, $C_1$-$C_3$ alkyl primary amine and $C_1$-$C_7$ dialkyl secondary amine are preferred. Amides of the compounds of the present disclosure can be prepared according to the conventional methods, for example, March's Advanced Organic Chemistry, 5 Edition, M. B. Smith & J. March, John Wiley & Sons, 2001.

The term "prodrug" refers to a compound that is rapidly converted in vivo to give the parent compound of the above formula, for example, by means of hydrolysis in the blood. For a detailed discussion, see T. Higuchi and V. Stella, "Pro-drugs as Novel Delivery Systems," Vol. 14 of the A. C. S, Symposium Series and Bioreversible Carriers in Drug Design, ed. Edward B, Roche, American Pharmaceutical Association and Pergamon Press, 1987, both of which were introduced herein as references.

"Subjects" to which administration is contemplated include, but are not limited to, humans (e.g., males or females of any age group, e.g., paediatric subjects (e.g., infants, children, adolescents) or adult subjects (e.g., young adults, middle-aged adults or older adults) and/or non-human animals, such as mammals, e.g., primates (e.g., cynomolgus monkeys, rhesus monkeys), cattle, pigs, horses, sheep, goats, rodents, cats and/or dogs. In some embodiments, the subject is a human. In some embodiments, the subject is a non-human animal. The terms "human", "patient" and "subject" can be used interchangeably herein.

"Disease," "disorder," and "condition" can be used interchangeably herein.

Unless indicated, otherwise the term "treatment" as used herein includes the effect on a subject who is suffering from a particular disease, disorder, or condition, which reduces the severity of the disease, disorder, or condition, or delays or slows the progression of the disease, disorder or condition ("therapeutic treatment"). The term also includes the effect that occurs before the subject begins to suffer from a specific disease, disorder or condition ("prophylactic treatment").

Generally, the "effective amount" of a compound refers to an amount sufficient to elicit a target biological response. As understood by those skilled in the art, the effective amount of the compound of the disclosure can vary depending on the following factors, such as the desired biological endpoint, the pharmacokinetics of the compound, the diseases being treated, the mode of administration, and the age, health status and symptoms of the subjects. The effective amount includes therapeutically effective amount and prophylactically effective amount.

Unless indicated, otherwise the "therapeutically effective amount" of the compound as used herein is an amount sufficient to provide therapeutic benefits in the course of treating a disease, disorder or condition, or to delay or minimize one or more symptoms associated with the disease, disorder or condition. The therapeutically effective amount of a compound refers to the amount of the therapeutic agent that, when used alone or in combination with other therapies, provides a therapeutic benefit in the treatment of a disease, disorder or condition. The term "therapeutically effective amount" can include an amount that improves the overall treatment, reduces or avoids the symptoms or causes of the disease or condition, or enhances the therapeutic effect of other therapeutic agents.

Unless indicated, otherwise the "prophylactically effective amount" of the compound as used herein is an amount sufficient to prevent a disease, disorder or condition, or an amount sufficient to prevent one or more symptoms associated with a disease, disorder or condition, or an amount sufficient to prevent the recurrence of a disease, disorder or condition. The prophylactically effective amount of a compound refers to the amount of a therapeutic agent that, when used alone or in combination with other agents, provides a prophylactic benefit in the prevention of a disease, disorder or condition. The term "prophylactically effective amount" can include an amount that improves the overall prevention, or an amount that enhances the prophylactic effect of other preventive agents.

"Combination" and related terms refer to the simultaneous or sequential administration of the compounds of the present disclosure and other therapeutic agents. For example, the compounds of the present disclosure cart be administered simultaneously or sequentially in separate unit dosage with other therapeutic agents, or simultaneously in a single unit dosage with other therapeutic agents.

DETAILED DESCRIPTION OF THE INVENTION

As used herein, "compounds of the present disclosure" refer to the compounds of formula (I) below, or pharmaceutically acceptable salts, enantiomers, diastereomers, racemates, solvates, hydrates, polymorphs, prodrugs or isotope variants thereof, and mixtures thereof.

Compounds are generally described herein using standard nomenclature. It should be understood, unless otherwise specified, that compounds with asymmetric center(s) include all optical isomers and mixtures thereof. Furthermore, unless otherwise specified, all isomer compounds and carbon-carbon double bonds included in the present disclosure may be in the form of Z and E. Compounds which exist in different tautomeric forms, one of which is not limited to any particular tautomer, but is intended to cover all tautomeric forms. The general formulas are used for certain compounds, including descriptions and variables. Unless otherwise specified, each variable in such formula is defined independently of any other variable and multiple variables that independently define any one of the variables at each occurrence.

In one embodiment, the present disclosure is directed to the compound of general formula (I), or pharmaceutically acceptable salts, enantiomers, diastereomers, racemates, solvates, hydrates, polymorphs, prodrugs or isotope variants thereof, and mixtures thereof:

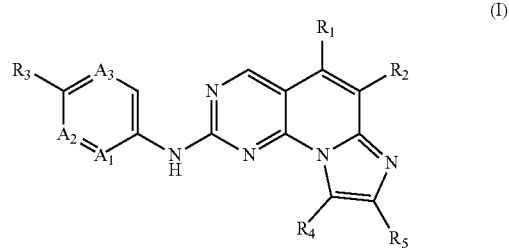

(I)

wherein:

$A_1$ is selected from $CR_3$ or N;

$A_2$ is selected from $CR_3$;

$A_3$ is selected from $CR_3$;

$R_1$ is hydrogen;

$R_2$ is selected from hydrogen, halogen, —CN, —$OR_a$, —$SR_a$, —$NR_bR_c$, —$C(O)R_a$, —$C(O)OR_a$, —$C(O)NR_bR_c$, $C_{1-6}$alkyl or $C_{1-6}$haloalkyl;

$R_3$ is selected from hydrogen, halogen, —CN, —$NO_2$, —$OR_a$, —$SR_a$, —$NR_bR_c$, —O—$C_{1-6}$ alkylene-$R_6$, $C_{1-6}$ alkyl, $C_{1-6}$ haloalkyl, -L'-$C_{3-7}$ cycloalkyl, -L'-3- to 11-membered heterocyclyl, -L'-$C_{6-10}$ aryl or -L'-5- to 10-membered heteroaryl, said groups are optionally substituted with 1, 2, 3, 4 or 5 $R_6$ groups;

$R_4$ is selected from hydrogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_5$ is hydrogen;

$R_6$ is selected from hydrogen, —$NH_2$, —$NHC_{1-6}$ alkyl, —$N(C_{1-6}$alkyl$)_2$, $C_{1-6}$alkyl or $C_{1-6}$haloalkyl;

or two $R_6$ groups on a same carbon atom are taken together to form oxo or thioxo;

wherein:

$R_4$ is optionally substituted with 1, 2 or 3 R' groups, wherein R' is independently selected from hydrogen, halogen, —CN, —$NO_2$, —$OR_a$, —$SR_a$, —$NR_bR_c$, —$C(O)OR_a$, —$C(O)NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;

$R_a$ is independently selected from hydrogen, $C_{1-6}$ alkyl, $C_{2-6}$ alkenyl, $C_{2-6}$ alkynyl or $C_{1-6}$ haloalkyl;

$R_b$ and $R_c$ are independently selected from hydrogen, $C_{1-6}$ alkyl, $C_{2-6}$ alkenyl, $C_{2-6}$ alkynyl or $C_{1-6}$ haloalkyl; or $R_b$, $R_c$ and N atom are taken together to form a 3- to 7-membered heterocyclyl;

L' is selected from a chemical bond or —O—.

$A_1$, $A_2$ and $A_3$

In one embodiment, $A_1$ is $CR_3$; in another embodiment, $A_1$ is CH; in another embodiment, $A_1$ is N.

In one embodiment, $A_2$ is $CR_3$; in another embodiment, $A_2$ is CH; in another embodiment, $A_2$ is $CR_{3b}$.

In one embodiment, $A_3$ is $CR_3$; in another embodiment, $A_3$ is CH; in another embodiment, $A_3$ is $CR_{3a}$.

$R_2$

In one embodiment, $R_2$ is hydrogen; in another embodiment, $R_2$ is halogen; in another embodiment, $R_2$ is —CN; in another embodiment, $R_2$ is —$OR_a$; in another embodiment, $R_2$ is —$SR_a$; in another embodiment, $R_2$ is —$NR_bR_c$; in another embodiment, $R_2$ is —$C(O)R_a$; in another embodiment, $R_2$ is —$C(O)OR_a$; in another embodiment, $R_2$ is —$C(O)NR_bR_c$; in another embodiment, $R_2$ is $C_{1-6}$alkyl; in another embodiment, $R_2$ is $C_{1-6}$ haloalkyl.

$R_3$

In one embodiment, $R_3$ is hydrogen; in another embodiment, $R_3$ is halogen; in another embodiment, $R_3$ is —CN; in another embodiment, $R_3$ is —$NO_2$; in another embodiment, $R_3$ is —$OR_a$; in another embodiment, $R_3$ is —$SR_a$; in another embodiment, $R_3$ is —$NR_bR_c$; in another embodiment, $R_3$ is —O—$C_{1-6}$ alkylene —$R_6$; in another embodiment, $R_3$ is $C_{1-6}$ alkyl; in another embodiment, $R_3$ is $C_{1-6}$ haloalkyl; in another embodiment, $R_3$ is -L'-$C_{3-7}$ cycloalkyl; in another embodiment, $R_3$ is -L'-3- to 11-membered heterocyclyl; in another embodiment, $R_3$ is -L'-3- to 9-membered heterocyclyl; in another embodiment, $R_3$ is -L'-$C_{6-10}$ aryl; in another embodiment, $R_3$ is -L'-5- to 10-membered heteroaryl.

In the embodiments of $R_3$ described above, the said groups are optionally substituted with 1, 2, 3, 4 or 5 $R_6$ groups. In one embodiment, the said groups are substituted with 1 $R_6$ group; in another embodiment, the said groups are substituted with 2 $R_6$ groups; in another embodiment, the said groups are substituted with 3 $R_6$ groups; in another embodiment, the said groups are substituted with 4 $R_6$ groups; in another embodiment, the said groups are substituted with 5 $R_6$ groups.

$R_4$

In one embodiment, $R_4$ is hydrogen; in another embodiment, $R_4$ is $C_{1-6}$ alkyl; in another embodiment, $R_4$ is $C_{1-6}$ haloalkyl; in another embodiment, $R_4$ is $C_{3-7}$ cycloalkyl; in another embodiment, $R_4$ is 3- to 7-membered heterocyclyl; in another embodiment, $R_4$ is $C_{6-10}$ aryl; in another embodiment, $R_4$ is 5- to 0-membered heteroaryl.

In the embodiments of $R_4$ described above, the said groups are optionally substituted with 1, 2 or 3 R' groups. In one embodiment, the said groups are substituted with 1 R' group; in another embodiment, the said groups are substituted with 2 R' groups; in another embodiment, the said groups are substituted with 3 R' groups.

In the embodiments described above, R' is hydrogen; in another embodiment, R' is halogen; in another embodiment, R' is —CN; in another embodiment, R' is —$NO_2$; in another embodiment, R' is —$OR_a$; in another embodiment, R' is —$SR_a$; in another embodiment, R' is —$NR_bR_c$; in another embodiment, R' is —$C(O)R_a$; in another embodiment, R' is —$C(O)OR_a$; in another embodiment, R' is —$C(O)NR_bR_c$; in another embodiment, R' is $C_{1-6}$ alkyl; in another embodiment, R' is $C_{1-6}$ haloalkyl; in another embodiment, R' is $C_{3-7}$cycloalkyl; in another embodiment, R' is 3- to 7-membered heterocyclyl; in another embodiment, R' is $C_{6-10}$ aryl; in another embodiment, R' is 5- to 10-membered heteroaryl.

$R_6$

In one embodiment, $R_6$ is hydrogen; in another embodiment, $R_6$ is —$NH_2$; in another embodiment, $R_6$ is —$NHC_{1-6}$alkyl; in another embodiment, $R_6$ is —$N(C_{1-6}$ alkyl$)_2$; in another embodiment, $R_6$ is $C_{1-6}$alkyl; in another embodiment, $R_6$ is $C_{1-6}$haloalkyl; in another embodiment, two $R_6$ groups on a same carbon atom are taken together to form oxo. In another embodiment, two $R_6$ groups on a same carbon atom are taken together to form thioxo.

L'

In one embodiment, L' is a chemical bond; in another embodiment, L' is —O—.

Any technical solution in any one of the above embodiments, or any combination thereof, may be combined with any technical solution in any one of the above embodiments, or any combination thereof. For example, any technical solution of $A_1$, or any combination thereof, may be combined with any technical solution of $A_2$, $A_3$, $R_1$-$R_6$, R', $R_a$, $R_b$, $R_c$, and L' or any combination thereof. The present disclosure is intended to include all combination of such technical solutions, which are not exhaustively listed here to save space.

In a more specific embodiment, the present disclosure provides a technical solution 1, which is a compound of general formula (II), or pharmaceutically acceptable salts, enantiomers, diastereomers, racemates, solvates, hydrates, polymorphs, prodrugs or isotope variants thereof, and mixtures thereof:

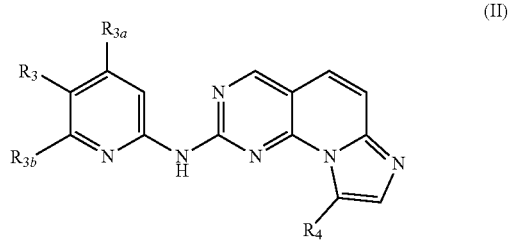

(II)

wherein:

$R_3$ is selected from

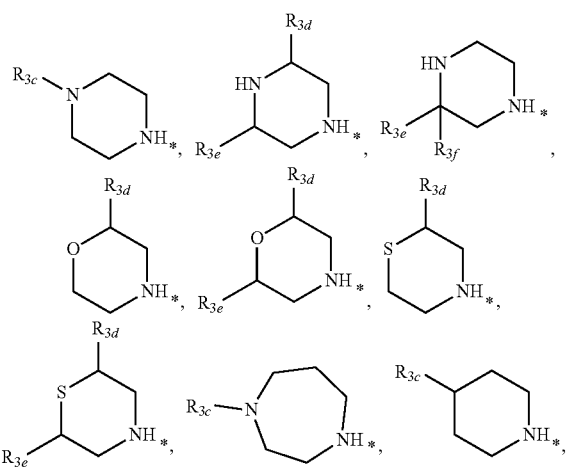

-continued

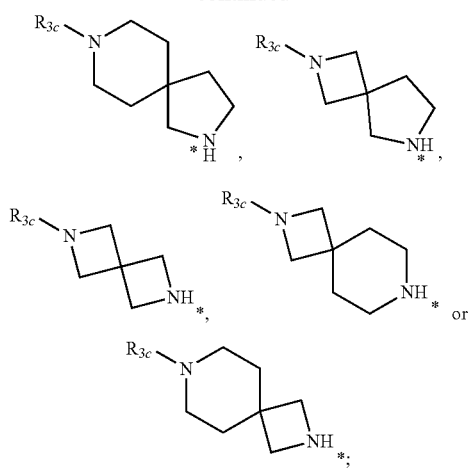

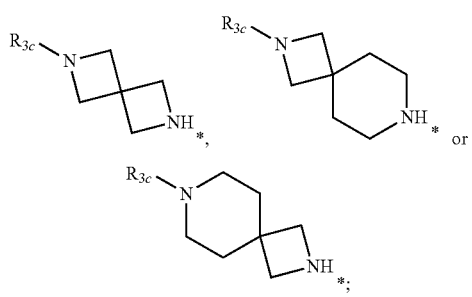

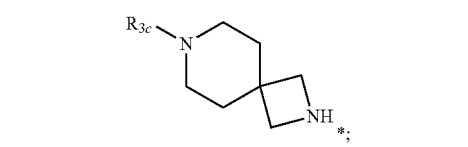

$R_{3a}$, $R_{3b}$, $R_{3c}$, $R_{3d}$, $R_{3e}$, and $R_{3f}$ are independently selected from hydrogen, halogen, —CN, —NO$_2$, C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl;

$R_4$ is selected from C$_{1-6}$ alkyl, C$_{1-6}$ haloalkyl, C$_{3-7}$ cycloalkyl or 3- to 7-membered heterocyclyl.

In another more specific embodiment, the present disclosure provides a technical solution 2, which relates to the compounds according to the technical solution 1, wherein $R_3$ is selected from

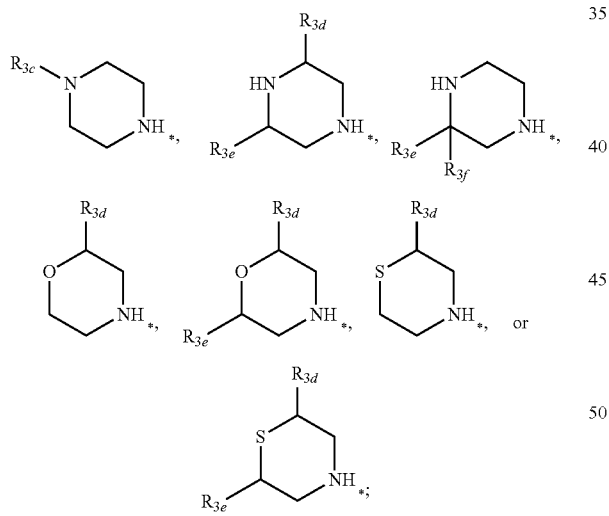

preferably, $R_3$ is selected from

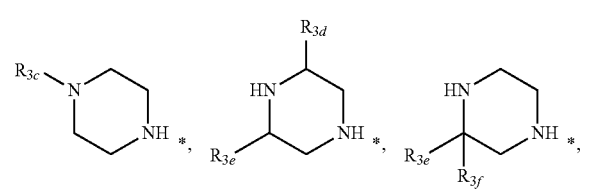

-continued

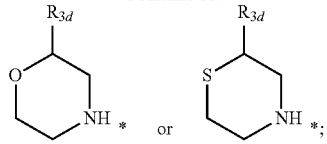

preferably, $R_3$ is selected from

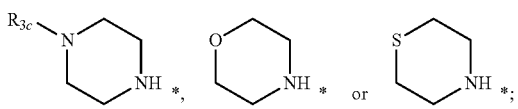

preferably, $R_3$ is selected from

preferably, $R_3$ is

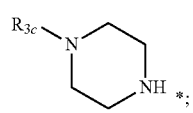

or, $R_3$ is selected from

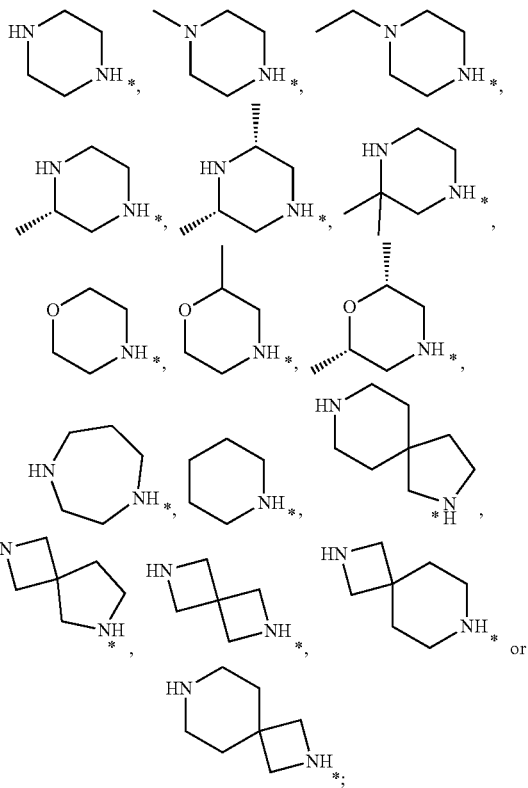

preferably, $R_3$ is selected from

[structures: piperazine, N-methylpiperazine, N-ethylpiperazine; stereochemistry variants; morpholine variants]

preferably, $R_3$ is selected from

[structures: piperazine, N-methylpiperazine, N-ethylpiperazine; stereochemistry variants; morpholine variants]

preferably, $R_3$ is selected from

[structures: piperazine or morpholine]

preferably, $R_3$ is

[structure: piperazine]

In another more specific embodiment, the present disclosure provides a technical solution 3, which relates to the compounds according to any one of the technical solutions 1 and 2, wherein $R_{3a}$, $R_{3b}$, $R_{3c}$, $R_{3d}$, $R_{3e}$ and $R_{3f}$ are independently selected from hydrogen, halogen, $C_{1-6}$alkyl or $C_{1-6}$haloalkyl;

preferably, $R_{3a}$, $R_{3b}$, $R_{3c}$, $R_{3d}$, $R_{3e}$, and $R_{3f}$ are independently selected from hydrogen, halogen or $C_{1-6}$alkyl;

preferably, $R_{3a}$ and $R_{3b}$ are independently selected from hydrogen, halogen or $C_{1-6}$alkyl; and $R_{3c}$, $R_{3d}$, $R_{3e}$, and $R_{3f}$ are independently selected from hydrogen or $C_{1-6}$alkyl;

preferably, $R_{3a}$ and $R_{3b}$ are independently selected from hydrogen, fluorine or methyl; and $R_{3c}$, $R_{3d}$, $R_{3e}$ and $R_{3f}$ are independently selected from hydrogen, methyl or ethyl;

preferably, $R_{3a}$ and $R_{3b}$ are independently selected from hydrogen, halogen or $C_{1-6}$alkyl;

preferably, $R_{3a}$ and $R_{3b}$ are independently selected from hydrogen, fluorine or methyl;

preferably, $R_{3a}$, $R_{3b}$ and $R_{3c}$, are independently selected from hydrogen, $C_{1-6}$alkyl, $C_{1-6}$haloalkyl, $C_{3-7}$cycloalkyl, 3- to 7-membered heterocyclyl, $C_{6-10}$ aryl or 5- to 10-membered heteroaryl, provided that at most one of $R_{3a}$, $R_{3b}$ and $R_{3c}$ is not hydrogen;

preferably, $R_{3a}$, $R_{3b}$ and $R_{3c}$ are independently selected from hydrogen, $C_{1-6}$alkyl or $C_{1-6}$haloalkyl, provided that at most one of $R_{3a}$, $R_{3b}$, and $R_{3c}$ is not hydrogen;

preferably, $R_{3a}$, $R_{3b}$ and $R_{3c}$, are independently selected from hydrogen or $C_{1-6}$alkyl, provided that at most one of $R_{3a}$, $R_{3b}$ and $R_{3c}$, is not hydrogen;

preferably, $R_{3a}$, $R_{3b}$ and $R_{3c}$, are independently selected from hydrogen, methyl or ethyl provided that at most one of $R_{3a}$, $R_{3b}$ and $R_{3c}$ is not hydrogen;

preferably, $R_{3a}$ and $R_{3b}$ are independently selected from hydrogen or $C_{1-6}$alkyl;

preferably, $R_{3a}$ and $R_{3b}$ are independently selected from hydrogen or methyl.

In another more specific embodiment, the present disclosure provides a technical solution 4, which relates to the compounds according to any one of the technical solutions 1 to 3, wherein $R_4$ is selected from $C_{1-6}$alkyl or $C_{3-7}$cycloalkyl;

preferably, $R_4$ is selected from isopropyl or cyclopentyl.

In a more specific embodiment, the present disclosure provides a technical solution 5, which is a compound of general formula (II), or pharmaceutically acceptable salts, enantiomers, diastereomers, racemates, solvates, hydrates, poly morphs, prodrugs or isotope variants thereof, and mixtures thereof:

(II)

[structure of general formula (II) with substituents $R_3$, $R_{3a}$, $R_{3b}$, $R_4$]

wherein:
$R_3$ is selected from

[structures: piperazine, morpholine, thiomorpholine, and stereochemistry variants of morpholine and thiomorpholine]

$R_{3a}$ and $R_{3b}$ are independently selected from hydrogen, halogen, —CN, —NO$_2$, $C_{1-6}$ alkyl, $C_{1-6}$haloalkyl, $C_{3-7}$cycloalkyl, 3- to 7-membered heterocyclyl, $C_{6-10}$ aryl or 5- to 10-membered heteroaryl;

$R_4$ is selected from $C_{1-6}$alkyl, $C_{1-6}$haloalkyl, $C_{3-7}$cycloalkyl or 3- to 7-membered heterocyclyl;

In another more specific embodiment, the present disclosure provides a technical solution 6, which relates to the compounds according to the technical solution 5, wherein
preferably, $R_3$ is selected from

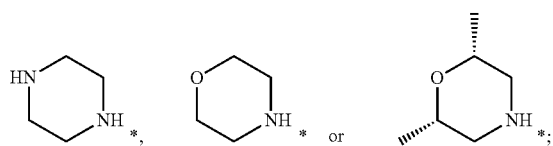

preferably, $R_3$ is selected from

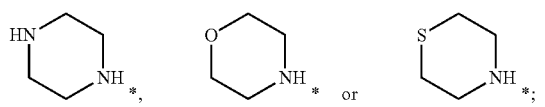

preferably, $R_3$ is selected from

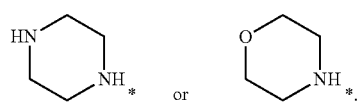

In another more specific embodiment, the present disclosure provides a technical solution 7, which relates to the compounds according to any one of the technical solutions 5 and 6, wherein $R_{3a}$ and $R_{3b}$ are independently selected from hydrogen, halogen, $C_{1-6}$ alkyl or $C_{1-6}$haloalkyl;
preferably, $R_{3a}$ and $R_{3b}$ are independently selected from hydrogen, $C_{1-6}$ alkyl, $C_{1-6}$haloalkyl, $C_{3-7}$ cycloalkyl, 3- to 7-membered heterocyclyl, $C_{6-10}$ aryl or 5- to 10-membered heteroaryl;
preferably, $R_{3a}$ and $R_{3b}$ are independently selected from hydrogen, halogen or $C_{1-6}$ alkyl;
preferably, $R_{3a}$ and $R_{3b}$ are independently selected from hydrogen, fluorine or methyl;
preferably, $R_{3a}$ and $R_{3b}$ are independently selected from hydrogen, $C_{1-6}$ alkyl or $C_{3-6}$ haloalkyl;
preferably, $R_{3a}$ and $R_{3b}$ are independently selected from hydrogen or $C_{1-6}$ alkyl;
preferably, $R_{3a}$ and $R_{3b}$ are independently selected from hydrogen or methyl;
preferably, $R_{3a}$ is hydrogen; and $R_{3b}$ is selected from hydrogen, $C_{1-6}$alkyl, $C_{1-6}$haloalkyl cycloalkyl, 3- to 7-membered heterocyclyl, $C_{6-10}$ aryl or 5- to 10-membered heteroaryl;
preferably, $R_{3a}$ is hydrogen; and $R_{3b}$ is selected from hydrogen, $C_{1-6}$alkyl or $C_{1-6}$haloalkyl;
preferably, $R_{3a}$ is hydrogen; and $R_{3b}$ is selected from hydrogen or $C_{1-6}$alkyl;
preferably, $R_{3a}$ is hydrogen; and $R_{3b}$ is selected from hydrogen or methyl.

In another more specific embodiment, the present disclosure provides a technical solution 8, which relates to the compounds according to any one of the technical solutions 5 to 7, wherein $R_4$ is selected from $C_{1-6}$alkyl or $C_{3-7}$cycloalkyl;
preferably, $R_4$ is selected from isopropyl or cyclopentyl.

In a more specific embodiment, the present disclosure provides a technical solution 9, which is a compound of general formula (II), or pharmaceutically acceptable salts, enantiomers, diastereomers, racemates, solvates, hydrates, poly morphs, prodrugs or isotope variants thereof, and mixtures thereof:

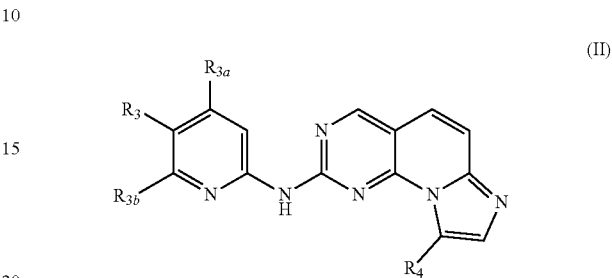

(II)

wherein:
$R_3$ is selected from

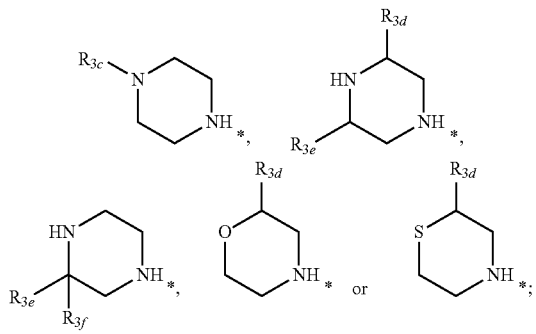

$R_{3a}$, $R_{3b}$, $R_{3c}$, $R_{3d}$, $R_{3e}$, and $R_{3f}$ are independently selected from hydrogen, halogen, —CN, —NO$_2$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl;
$R_4$ is selected from $C_{1-6}$alkyl, $C_{1-6}$haloalkyl $C_{3-7}$cycloalkyl or 3- to 7-membered heterocyclyl.

In another more specific embodiment, the present disclosure provides a technical solution 10, which relates to the compounds according to the technical solution 9, wherein
$R_3$ is selected from

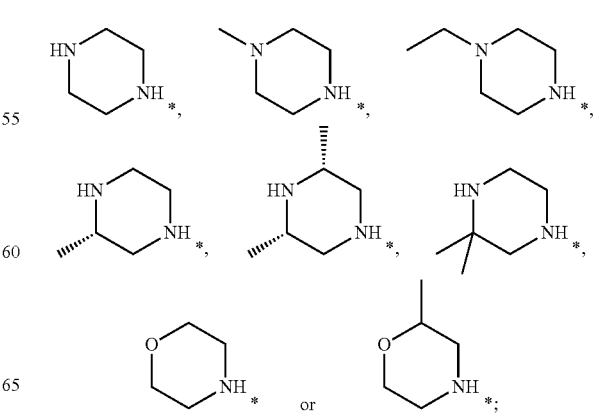

preferably, $R_3$ is

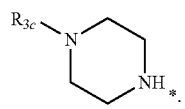

In another more specific embodiment, the present disclosure provides a technical solution 11, which relates to the compounds according to any one of the technical solutions 9 and 10, wherein $R_{3a}$, $R_{3b}$, $R_{3c}$, $R_{3d}$, $R_{3e}$ and $R_{3f}$ are independently selected from hydrogen, halogen, $C_{1-6}$alkyl or $C_{1-6}$ haloalkyl;

preferably, $R_{3a}$, $R_{3b}$, $R_{3c}$, $R_{3d}$, $R_{3e}$, and $R_{3f}$ are independently selected from hydrogen, halogen or $C_{1-6}$ alkyl;

preferably, $R_{3a}$ and $R_{3b}$ are independently selected from hydrogen, halogen or $C_{1-6}$alkyl; and $R_{3c}$, $R_{3d}$, $R_{3e}$, and $R_{3f}$ are independently selected from hydrogen or $C_{1-6}$alkyl;

preferably, $R_{3a}$ and $R_{3b}$ are independently selected from hydrogen, fluorine or methyl; and $R_{3c}$, $R_{3d}$, $R_{3e}$ and $R_{3f}$ are independently selected from hydrogen, methyl or ethyl;

preferably, $R_{3a}$ and $R_{3b}$ are independently selected from hydrogen, halogen or $C_{1-6}$ alkyl;

preferably, $R_{3a}$ and $R_{3b}$ are independently selected from hydrogen, fluorine or methyl;

preferably, $R_{3a}$, $R_{3b}$, $R_{3c}$, $R_{3d}$, $R_{3e}$, and $R_{3f}$ are independently selected from hydrogen, $C_{1-6}$alkyl, $C_{1-6}$ haloalkyl, $C_{3-7}$cycloalkyl, 3- to 7-membered heterocyclyl, $C_{6-10}$ aryl or 5- to 10-membered heteroaryl;

preferably, $R_{3a}$, $R_{3b}$, $R_{3c}$, $R_{3d}$, $R_{3e}$ and $R_{3f}$ are independently selected from hydrogen, $C_{1-6}$alkyl or $C_{1-6}$haloalkyl;

preferably, $R_{3a}$, $R_{3b}$, $R_{3c}$, $R_{3d}$, $R_{3e}$ and $R_{3f}$ are independently selected from hydrogen or $C_{1-6}$alkyl;

preferably, $R_{3a}$ and $R_{3b}$ are independently selected from hydrogen or $C_{1-6}$alkyl; and $R_{3c}$, $R_{3d}$, $R_{3e}$ and $R_{3f}$ are independently selected from hydrogen or $C_{1-6}$alkyl;

preferably, $R_{3a}$ and $R_{3b}$ are independently selected from hydrogen or methyl; and $R_{3c}$, $R_{3d}$, $R_{3e}$, and $R_{3f}$ are independently selected from hydrogen, methyl or ethyl;

preferably, $R_{3a}$ and $R_{3b}$ are independently selected from hydrogen or $C_{1-6}$alkyl;

preferably, $R_{3a}$ and $R_{3b}$ are independently selected from hydrogen or methyl;

preferably, $R_{3a}$, $R_{3b}$ and $R_{3c}$ are independently selected from hydrogen, $C_{1-6}$alkyl, $C_{1-6}$haloalkyl, $C_{3-7}$cycloalkyl, 3- to 7-membered heterocyclyl, $C_{6-10}$ aryl or 5- to 10-membered heteroaryl, provided that at most one of $R_{3a}$, $R_{3b}$ and $R_{3c}$ is not hydrogen;

preferably, $R_{3a}$, $R_{3b}$ and $R_{3c}$ are independently selected from hydrogen, $C_{1-6}$alkyl or $C_{1-6}$haloalkyl, provided that at most one of $R_{3a}$, $R_{3b}$ and $R_{3c}$ is not hydrogen;

preferably, $R_{3a}$, $R_{3b}$ and $R_{3c}$ are independently selected from hydrogen or $C_{1-6}$alkyl, provided that at most one of $R_{3a}$, $R_{3b}$ and $R_{3c}$ is not hydrogen;

preferably, $R_{3a}$, $R_{3b}$ and $R_{3c}$ are independently selected from hydrogen, methyl or ethyl, provided that at most one of $R_{3a}$, $R_{3b}$ and $R_{3c}$ is not hydrogen;

preferably, $R_{3a}$ and $R_{3b}$ are hydrogen; and $R_{3c}$ is $C_{1-6}$alkyl, $C_{1-6}$haloalkyl, $C_{3-7}$cycloalkyl, 3- to 7-membered heterocyclyl, $C_{6-10}$ aryl or 5- to 10-membered heteroaryl;

preferably, $R_{3a}$ and $R_{3b}$ are hydrogen; and $R_{3c}$ is $C_{1-6}$alkyl or $C_{1-6}$haloalkyl;

preferably, $R_{3a}$ and $R_{3b}$ are hydrogen; and $R_{3c}$ is $C_{1-6}$alkyl;

preferably, $R_{3a}$ and $R_{3b}$ are hydrogen; and $R_{3c}$ is selected from methyl or ethyl.

In another more specific embodiment, the present disclosure provides a technical solution 12, which relates to the compounds according to any one of the technical solutions 9 to 11, wherein $R_4$ is selected from $C_{1-6}$alkyl or $C_{3-7}$cycloalkyl;

preferably, $R_4$ is selected from isopropyl or cyclopentyl.

In a more specific embodiment, the present disclosure provides a technical solution 13, which is a compound of general formula (III), or pharmaceutically acceptable salts, enantiomers, diastereomers, racemates, solvates, hydrates, polymorphs, prodrugs or isotope variants thereof, and mixtures thereof:

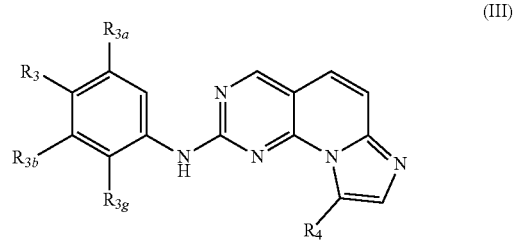

(III)

wherein:

$R_3$ is selected from —O—$C_{1-6}$ alkylene-$R_6$ or -L'-5- to 6-membered heterocyclyl, the said groups are optionally substituted with 1 or 2 $R_6$ groups;

$R_{3a}$, $R_{3b}$ and $R_{3c}$ are independently selected from hydrogen, halogen, $C_{1-6}$alkyl or —OR$_a$;

$R_a$ is selected from hydrogen or $C_{1-6}$ alkyl;

$R_6$ is independently selected from hydrogen, —NH$_2$, —NHC$_{1-6}$ alkyl, —N(C$_{1-6}$ alkyl)$_2$, $C_{1-6}$ alkyl or $C_{1-6}$haloalkyl;

L' is a chemical bond or —O—;

or $R_3$ and $R_{3b}$ are taken together to form an optionally substituted 5- to 6-membered heterocyclyl or 5- to 6-membered heteroaryl;

preferably, $R_3$ is selected from

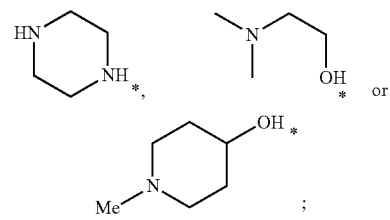

$R_{3a}$, $R_{3b}$ and $R_{3c}$ are independently selected from hydrogen, fluorine and OMe;

or $R_3$ and $R_{3b}$ are taken together to form

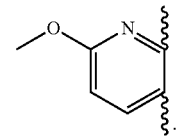

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate," The present disclosure encompasses all solvates of the compounds of the present disclosure.

The term "solvate" refers to forms of a compound or a salt thereof, which are associated with a solvent, usually by a solvolysis reaction. This physical association may include hydrogen bonding, Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R-x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R.0.5 $H_2O$)) and polyhydrates (x is a number greater than 1, for example, dihydrates (R.2 $H_2O$) and hexahydrates (R.6 $H_2O$)).

Compounds of the present disclosure may be in an amorphous or a crystalline form (polymorph). Furthermore, the compounds of the present disclosure may exist in one or more crystalline forms, Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^3H$ and $^{14}C$), can be used for the measurement of the distribution of drug and/or substrate in tissue. Tritium, which is $^3H$ and carbon-14, which is $^{14}C$ isotope, are particularly preferred, because they are easy to prepare and detect. Furthermore, replaced by heavier isotopes, such as deuterium, which is $^2H$, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A. C. S. Symposium Series, Vol. 14, Edward B. Roche, ed., Bioreversible Carriers in Drug Design, American Pharmaceutical Association and Pergamon Press, 1987, and D. Fleisher, S. Ramon and H. Barbra "Improved oral drug delivery: solubility limitations overcame by the use of prodrugs", Advanced Drug Delivery Reviews (1996) 19(2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, far example, compounds of the present disclosure wherein the hydroxyl, amino or sulfhydryl groups are banded to any group that, when administered to a patient, cleaves to form the hydroxyl, amino or sulfhydryl groups. Thus, representative examples of prodrugs include (but are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

The present disclosure also provides a pharmaceutical formulation comprising a therapeutically effective amount of a compound of formula (I), or therapeutically acceptable salts thereof, and pharmaceutically acceptable carriers, diluents or excipients thereof. All of these forms belong to the present disclosure.

Preferred compounds of the present disclosure include, but are not limited to the compounds listed below:

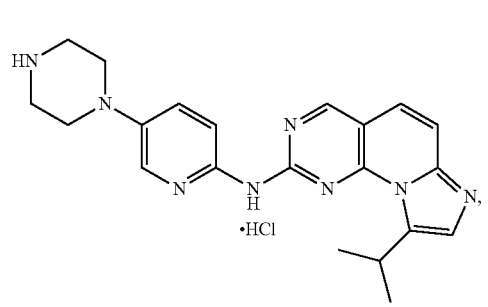

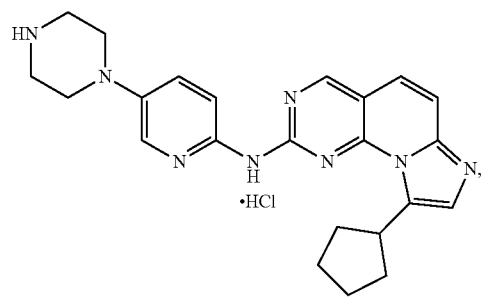

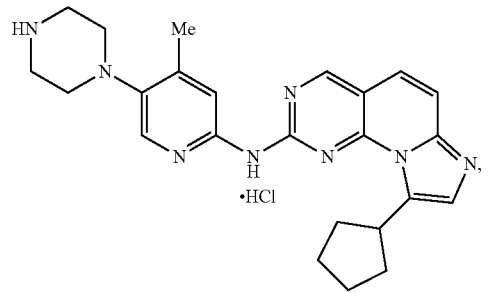

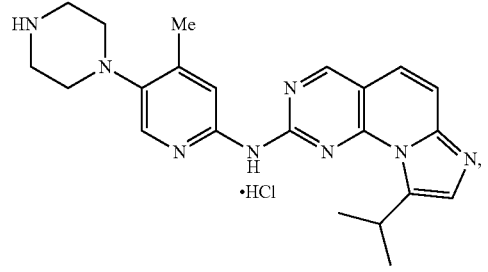

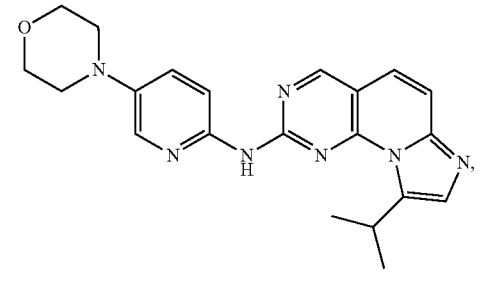

-continued

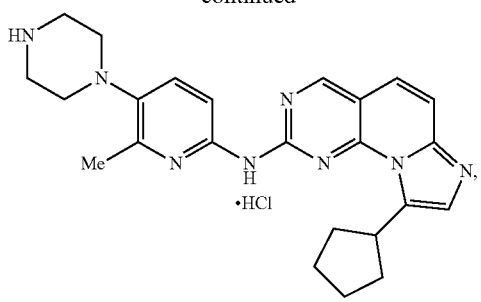

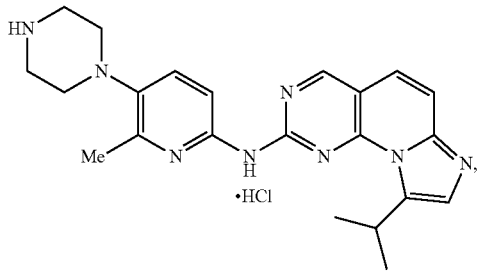

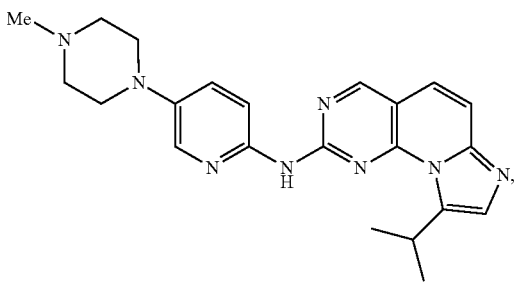

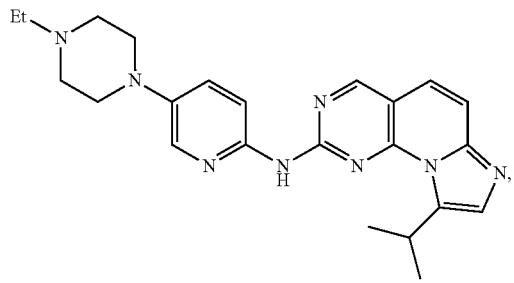

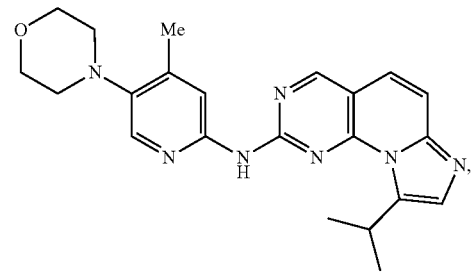

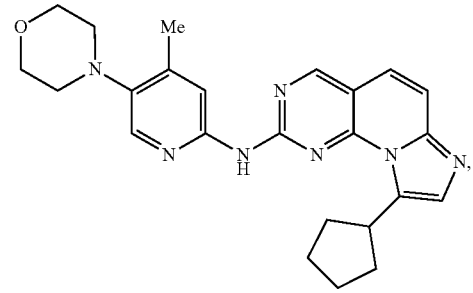

29
-continued
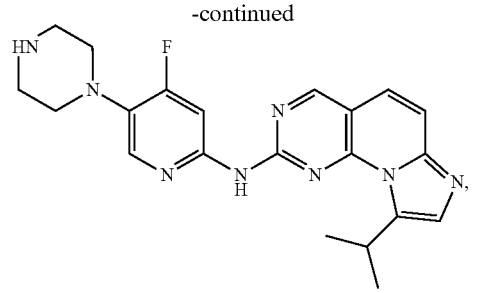
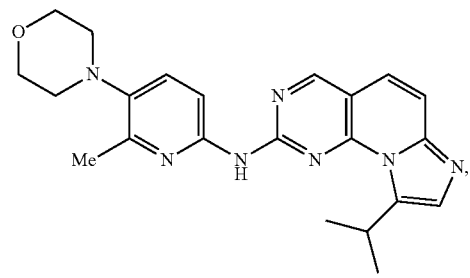
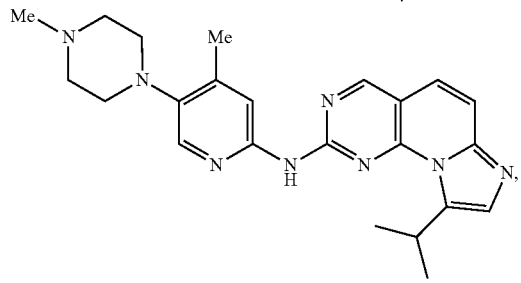
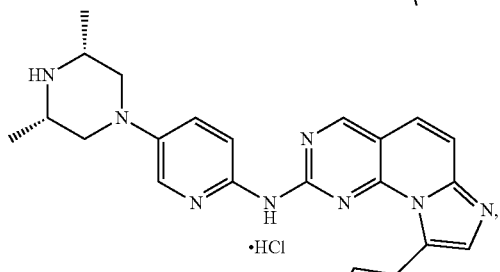
·HCl
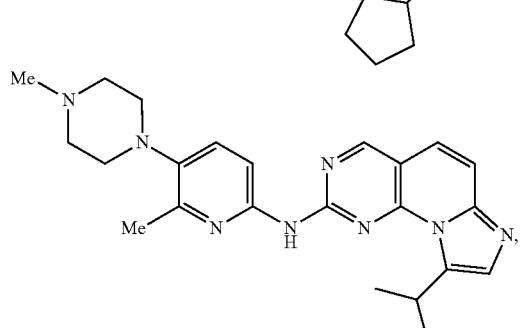
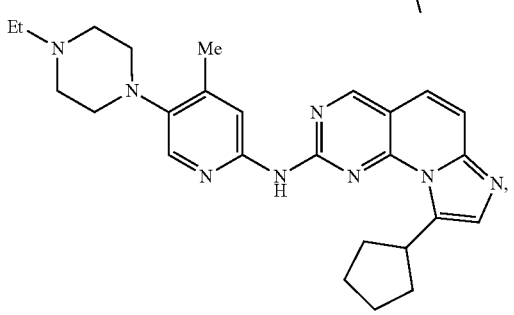
30
-continued
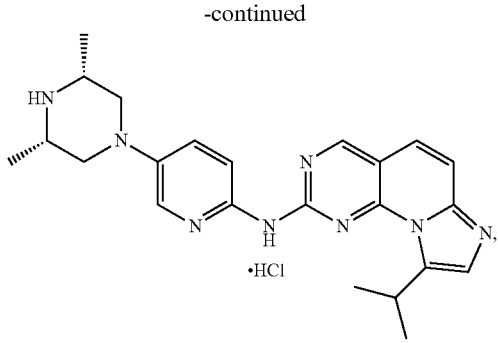
·HCl
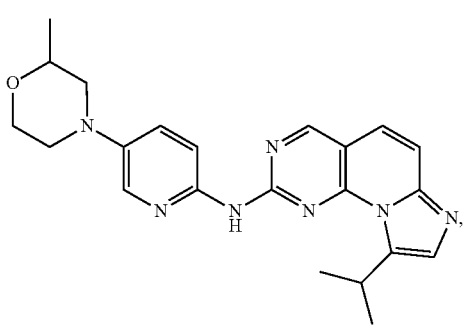
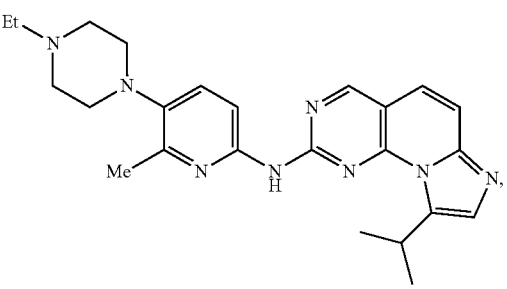
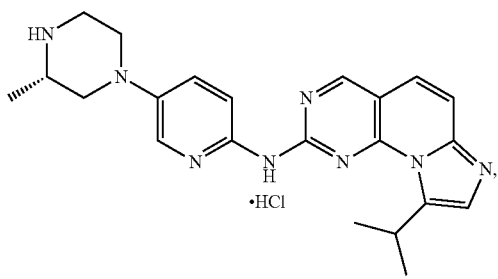
·HCl
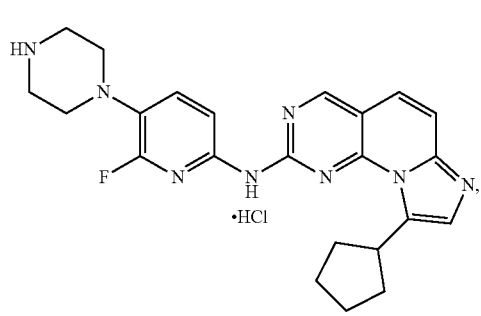
·HCl 31
-continued
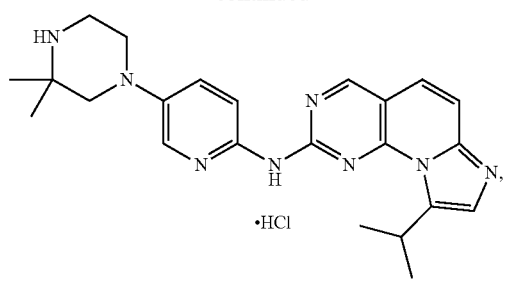
·HCl
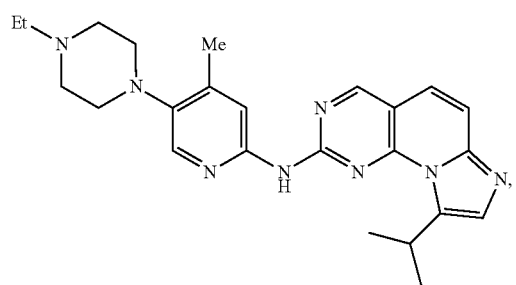
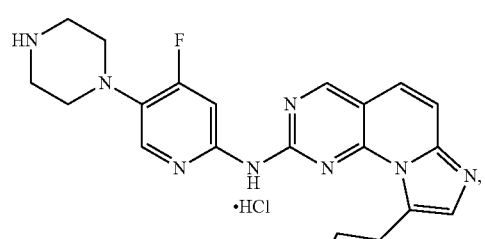
·HCl
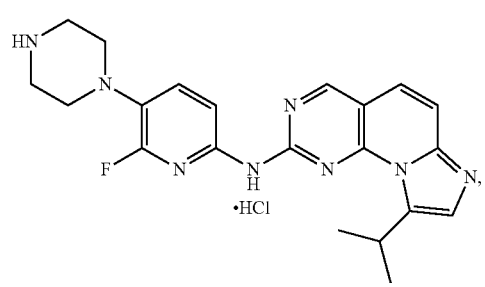
·HCl
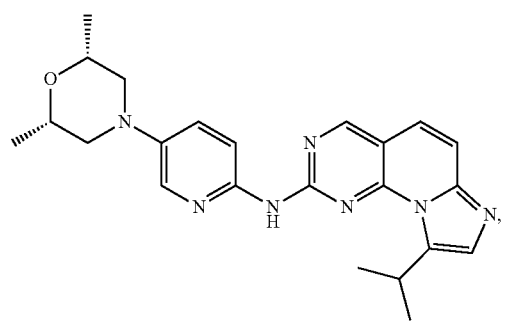
32
-continued
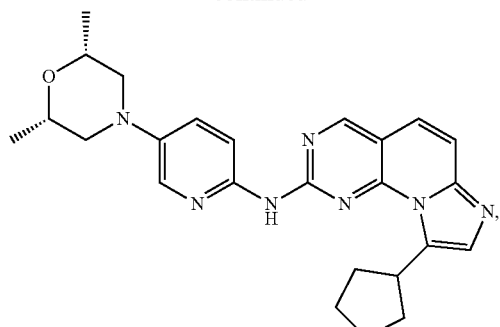
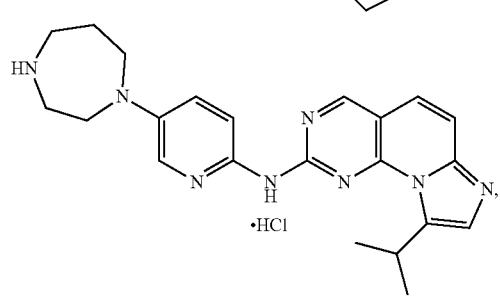
·HCl
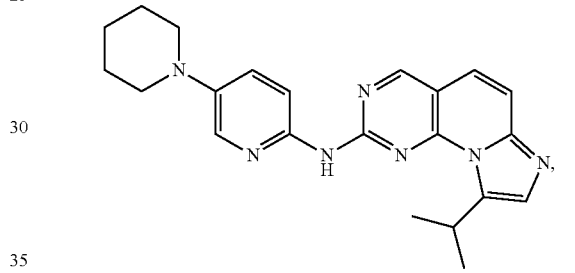
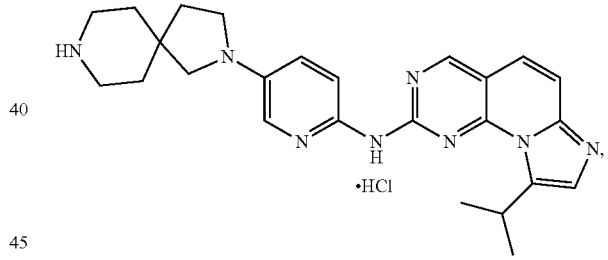
·HCl
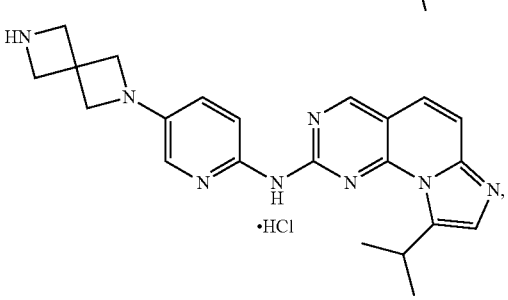
·HCl

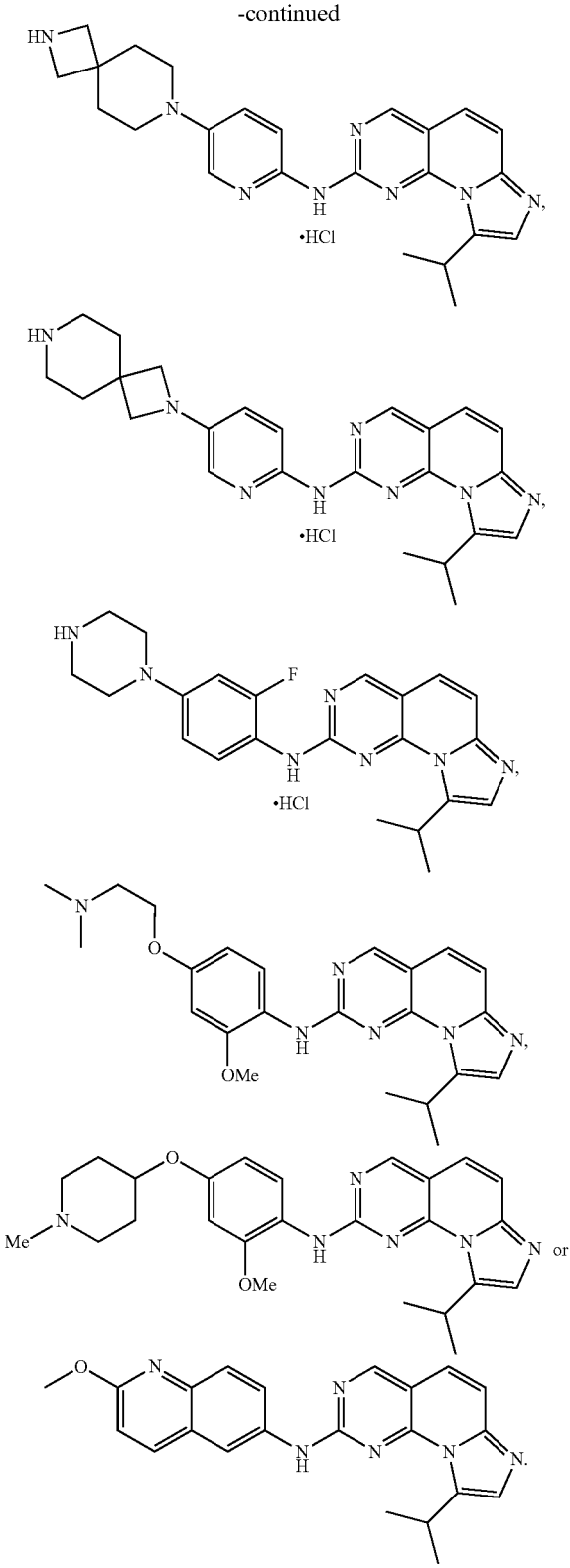

Pharmaceutical Compositions, Formulations and Kits

In another aspect, the present disclosure provides a pharmaceutical composition comprising a compound of the present disclosure (also referred to as the "active ingredient") and pharmaceutically acceptable excipients. In some embodiments, the pharmaceutical composition comprises an effective amount of the compound of the present disclosure. In some embodiments, the pharmaceutical composition comprises a therapeutically effective amount of the compound of the present disclosure. In some embodiments, the pharmaceutical composition comprises a prophylactically effective amount of the compound of the present disclosure.

Pharmaceutically acceptable excipients for use in the present disclosure refer to the non-toxic carriers, adjuvants or vehicles, which do not destroy the pharmacological activity of the compounds formulated together. Pharmaceutically acceptable carriers, adjuvants, or vehicles that can be used in the compositions of the present disclosure include (but are not limited to) ion exchangers, alumina, aluminum stearate, lecithin, serum proteins (such as human serum proteins), buffer substances (such as phosphate), glycine, sorbic acid, potassium sorbate, mixture of partial glycerides of saturated plant fatty acids, water, salts or electrolytes (such as protamine sulfate), disodium hydrogen phosphate, potassium hydrogen phosphate, sodium chloride, zinc salts, silica gel, magnesium trisilicate, polyvinyl pyrrolidone, cellulose-based substance, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). The kits provided may include a compound of the present disclosure, other therapeutic agent(s), and a first and a second containers (e.g., vials, ampoules, bottles, syringes, and/or dispersible packages or other suitable containers) containing the compound of the present disclosure and other therapeutic agent(s). In some embodiments, the provided kits can also optionally include a third container containing a pharmaceutically acceptable excipient for diluting or suspending the compound of the present disclosure and/or other therapeutic agent(s). In some embodiments, the compound of the present disclosure provided in the first container and other therapeutic agent(s) provided in the second container are combined to form a unit dosage form.

Administration

The pharmaceutical composition provided by the present disclosure can be administered by a variety of routes including, but not limited to, oral administration, parenteral administration, inhalation administration, topical administration, rectal administration, nasal administration, buccal administration, vaginal administration, administration by implant or other means of administration. For example, parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the route of administration selected, the actual compound administered, the age, weight and response of the individual patient, the severity of the patient's symptoms, etc.

When used to prevent the conditions described in the present disclosure, the compounds provided herein will be administered to a subject at risk of developing the conditions, typically based on the physician's recommendation and administered under the supervision of the physician, at the dosage level described above. Subjects at risk of developing the particular conditions generally include those who have a family history of the conditions, or those who have been identified by genetic testing or screening to be particularly susceptible to developing the conditions.

The pharmaceutical compositions provided herein can also be administered chronically ("chronic administration"). Chronic administration refers to the administration of a compound or pharmaceutical composition thereof for a long period of time, for example, 3 months, 6 months, 1 year, 2 years, 3 years, 5 years, etc., or can be continuously administered indefinitely, for example, for the rest of the subject's life. In some embodiments, the chronic administration is intended to provide a constant level of the said compound in the blood over a long period of time, for example, within the therapeutic window.

Pharmaceutical compositions of the present disclosure can be further delivered using various dosing methods. For example, in some embodiments, pharmaceutical compositions can be administered by bolus injection, for example, to increase the concentration of the compound in the blood to an effective level. The bolus dose depends on the desired systemic level of the active ingredient throughout the body, for example, intramuscular or subcutaneous bolus dose allows a slow release of the active ingredient, while the bolus that is delivered directly to the vein (e.g., via IV intravenous drip) allows a much faster delivery which quickly raises the concentration of the active ingredient in the blood to an effective level. In other embodiments, pharmaceutical compositions can be administered in a form of continuous infusion, for example, via IV intravenous drip, thereby providing a steady state concentration of the active ingredient in the subject's body. Moreover, in other embodiments, a bolus dose of the pharmaceutical compositions can be administered first followed by continuous infusion.

The compositions for oral administration can be in the form of bulk liquid solution or suspension or hulk powder. More commonly, however, in order to facilitate the precise dosing, the compositions are provided in unit dosage form. The term "unit dosage form" refers to physical discrete units suitable as unitary dosages for human patients and other mammals, each unit containing a predetermined quantity of active ingredient calculated to produce the desired therapeutic effects with suitable pharmaceutical excipients. Typical unit dosage forms include pre filled, pre-measured ampoules or syringes of the liquid compositions, or pills, tablets, capsules, etc. in the case of solid compositions. In such compositions, the said compound generally will be the minor component (about 0.1 to about 50% by weight, or preferably about 1 to about 40% by weight), with the remainder being various carriers or excipients and processing aids useful for forming the desired dosing form.

For oral dosage, a representative scheme is one to five, especially two to four, and typically three oral doses per day. Using these dosing patterns, each dose provides from about 0.01 to about 20 mg/kg of the compound of the present disclosure, with preferred doses each providing from about 0.1 to about 10 mg/kg, and especially from about 1 to about 5 mg/kg.

Transdermal doses are generally selected to provide similar or lower blood levels than are achieved using injection doses, usually in an amount of from about 0.01 to about 20% by weight, preferably from about 0.1 to about 20% by weight, preferably from about 0.1 to about 10% by weight, and more preferably from about 0.5 to about 15% by weight.

The injection dose level ranges from about 0.1 mg/kg/hr to at least 10 mg/kg/hr, all for from about 1 to about 120 hours, especially from 24 to 96 hours. In order to achieve a sufficient level of steady state, a preloading bolus of from about 0.1 mg/kg to about 10 mg/kg or more can also be administered. For human patients of 40 to 80 kg, the maximum total dose should not exceed approximately 2 g/day.

Liquid forms suitable for oral administration may include suitable aqueous or nonaqueous carriers, buffers, suspending agents and dispersants, coloring agents, flavoring agents, etc. Solid forms may include, for example, any of the following components, or compounds having the similar properties: binders, for example, microcrystalline cellulose, tragacanth gum or gelatin; excipients, for example, starch or lactose; disintegrants, for example, alginic acid, Primogel or corn starch; lubricants, for example, magnesium stearate; glidants, for example, colloidal silica; sweeteners, for example, sucrose or saccharin; or flavoring agents, for example, peppermint, methyl salicylate or orange flavouring.

Injectable compositions are typically based on the injectable sterile saline or phosphate-buffered saline, or other injectable excipients known in the art. As previously mentioned, in such compositions, the active ingredients will typically be the minor component, often from about 0.05 to 10% by weight, with the remainder being injectable excipients, etc.

The transdermal compositions are typically formulated as topical ointments or creams containing the active ingredients. When formulated as an ointment, the active ingredients are typically combined with paraffin or water miscible ointment base. Alternatively, the active ingredients can be formulated as a cream with, for example, oil-in-water cream base. Such transdermal formulations are well-known in the art and generally include other ingredients for enhancing stable skin penetration of the active ingredients or the formulations. All such known transdermal formulations and components are included within the scope of the present disclosure.

The compounds of the present disclosure may also be administered by transdermal devices. Thus, transdermal administration can be accomplished using a patch either of reservoir or porous membrane type, or of a plurality of solid substrates.

The above components of the compositions for oral administration, injection or topical administration are only representative. Other materials and processing techniques, etc., are described in the Section 8 of Remington's Pharmaceutical Sciences, 17th edition, 1985, Mack Publishing Company, Easton, Pa., which is incorporated herein by reference.

Compounds of the present disclosure may also be administered in a sustained release form or from a sustained release delivery system. Description of the representative sustained release materials can be found in Remington's Pharmaceutical Sciences.

The present disclosure also relates to pharmaceutically acceptable formulations of the compounds of the present disclosure. In one embodiment, the formulation comprises water. In another embodiment, the formulation comprises cyclodextrin derivative. The most common cyclodextrins are alpha-, beta- and gamma-cyclodextrins consisting of 6, 7 and 8 alpha-1,4-linked glucose units, respectively, optionally including one or more substituents on the linked sugar moiety, including, but are not limited to, methylated, hydroxyalkylated, acylated, and sulfoalkyl ether substitution. In some embodiments, the cyclodextrin is sulfoalkyl ether beta-cyclodextrin, e.g., sulfobutyl ether beta-cyclodextrin, also known as Captisol. See, for example, U.S. Pat. No. 5,376,645. In some embodiments, the formulation comprises hexapropyl-β-cyclodextrin (e.g., 10-50% in water).

Treatment

The present disclosure provides the methods for treating the following disorders or conditions in mammals (including humans): cell proliferative disorders, e.g. cancer, vascular smooth muscle hyperplasia associated with atherosclerosis, postoperative vascular stenosis, restenosis, and endometriosis; infections, including viral infections, e.g. DNA viruses such as herpes, and RNA viruses such as HIV, and fungal infections; autoimmune diseases, e.g. psoriasis and inflammation, such as rheumatoid arthritis, lupus, type I diabetes, diabetic nephropathy, multiple sclerosis and glomerulonephritis, organ transplant rejection, including host versus graft disease. The methods comprise administering to the mammal a therapeutically effective amount of a compound of the present disclosure or a composition thereof.

The present disclosure further provides compounds of the present disclosure useful for the treatment of abnormal cell proliferation, such as cancer. The present disclosure further provides a method of treating abnormal cell proliferation, such as cancers selected from the following: breast, ovary, cervix, prostate, testis, esophagus, stomach, skin, lung, bone, colon, pancreas, thyroid, biliary tract, buccal cavity and pharynx (mouth), lips, tongue, oral cavity, pharynx, small intestine, colorectal, large intestine, rectum, cancer of brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder cancer, liver cancer, kidney cancer, hone marrow disorder, lymphatic disorder, Hodgkin's disease, hairy cell carcinoma and leukemia, comprising administering to the subjects in need of such treatment a therapeutically effective amount of a compound of the present disclosure or a composition thereof.

Further, the present disclosure relates to a method of treating a subject having a disease caused by proliferation of vascular smooth muscle cells. Compounds of the present disclosure effectively inhibit the proliferation and migration of vascular smooth muscle cells. The method comprises administering to the subject in need of the treatment a compound of the present disclosure or a composition thereof in an amount sufficient to inhibit the proliferation and/or migration of the vascular smooth muscle.

The present disclosure further provides a method of treating a subject suffering from gout, comprising administering to the subject in need of treatment a compound of the present disclosure or a composition thereof in an amount sufficient to treat the condition.

The present disclosure further provides a method of treating a subject having a renal disease, such as a polycystic kidney disease, comprising administering to the subject in need of treatment an amount of a compound of the present disclosure or a composition thereof in an amount sufficient to treat the condition.

Due to their inhibitory activity against CDK (and other kinases, the compounds of the present disclosure are also useful research tools for studying the mechanism of action of these kinases in vitro and in vivo.

Compounds of the present disclosure are useful in the treatment of cancers (e.g., leukemia and cancers of lung, breast, prostate and skin, such as melanoma) and other proliferative diseases including, but are not limited to, psoriasis, HSV, HIV, restenosis, and atherosclerosis. In order to treat cancers using a compound of the present disclosure, a therapeutically effective amount of a pharmaceutically acceptable composition comprising at least one compound of the present disclosure is administered to the patient in need of such treatment, for example, who has cancer or another proliferative disorder.

The effective amount of a compound of the present disclosure is generally administered in a single or multiple doses at an average daily dose of from 0.01 mg to 50 mg of the compound per kilogram of patient's body weight, preferably from 0.1 mg to 25 mg of the compound per kilogram of patient's body weight. Generally, the compounds of the present disclosure may be administered to the patient in need of such treatment in a daily dosage ranges from about 1 mg to about 3500 mg per patient, preferably from 10 mg to 1000 mg. For example, the daily dosage per patient can be 10, 20, 30, 40, 50, 60, 70, 80, 90, 100, 150, 200, 250, 300, 350, 400, 500, 600, 700, 800, 900 or 1000 mg. It can be administered one or more times daily, weekly (or at intervals of several days) or on an intermittent schedule. For example, the compounds can be administered one or more times per day on a weekly basis (e.g., every Monday), continually or for several weeks, such as 4-10 weeks. Alternatively, the administration may be continued for several days (e.g., 2-10 days), followed by a few days (e.g., 1-30 days without administration of the compound, and the cycle may be repeated indefinitely or repeated for a given number of times, such as 4-10 cycles. For example, the compounds of the present disclosure may be administered daily for 5 days, then intermittently for 9 days, and then administered daily for 5 days, then intermittently for 9 days, and so on, repeating the cycle indefinitely or repeating 4-10 times.

Combination Therapy

Compounds or compositions of the present disclosure may be administered simultaneously with, prior to, or subsequent to one or more additional pharmaceutical agents, which may be useful as combination therapy. The pharmaceutical agents include therapeutically active agents. Pharmaceutical agents also include prophylactically active agents. Pharmaceutical agents include small organic molecules such as pharmaceutical compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nuclear proteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In some embodiments, the additional pharmaceutical agent is a pharmaceutical agent for treating and/or preventing the diseases described herein. Each additional pharmaceutical agent can be administered at a dose and/or on a time schedule determined by the pharmaceutical agent. The additional pharmaceutical agents may also be administered together with each other and/or with the compounds or compositions described herein, in a single dose, or administered separately in different doses. Specific combinations employed in this regimen will take into account the compatibility of the compounds of the present disclosure with the additional pharmaceutical agent(s) and/or the desired therapeutic and/or prophylactic effects to be achieved. Generally, it is expected that the additional pharmaceutical agent(s) utilized in combination be utilized at levels that do not exceed the levels at which they are utilized individually. In some embodiments, the levels used in combination will be lower than those utilized individually.

The additional pharmaceutical agents include, but are not limited to, anti-proliferative agents, anticancer agents, anti-angiogenic agents, anti-inflammatory agents, immunosuppressants, antibacterial agents, antiviral agents, cardiovascular agents, lipid-lowering agents, anti-diabetic agents, anti-allergic agents, contraceptive agents and analgesics. In one embodiment, the additional pharmaceutical agent is an anti-proliferative agent. In one embodiment, the additional medicament is an anticancer agent. In one embodiment, the additional medicament is an anti-leukemia agent. In one embodiment, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (asparaginase erwinia chrysogenum), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methotrexate), MEXATE (methotrexate), MEXATE-AQ (methotrexate), Mitoxantrone Hydrochloride, MUSTARGEN (mechlorethamine hydrochloride), MYLERAN (busulfan), NEOSAR (cyclophosphamide), ONCASPAR (pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib) or combinations thereof. In one embodiment, the additional pharmaceutical agent is an anti-lymphoma drug. In one embodiment, the additional medicament is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine-I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (cytarabine liposome), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant intergeron alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomine), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vinblastine sulfate), ZEVALIN (ibritumomab tiuxetan), ZOLINZA (vorinostat) ZYDELIG (idelalisib) or combinations thereof. In one embodiment, the additional pharmaceutical agent is REVLIMID (lenalidomide), DACOGEN (decitabine) VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine) or combinations thereof. In one embodiment, the additional pharmaceutical agent is ABITREXATE (methotrexate), ABRAXANE (paclitaxel albumin stabilized nanoparticles), AC, AC-T, ADE, ADRIAMYCIN PFS (doxorubicin hydrochloride), ADRUCIL (fluorouracil) AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (carbatinib-s-malate), COSMEGEN (dactinomycin), CYFOS (ifosfamide), CYRAMZA (ramucirumab), CYTOSAR-U (cytarabine) CYTOXAN (cyclophosphamide), DACOGEN (decitabine), DEGARELIX, DOXIL (doxorubicin hydrochloride liposome), Doxorubicin Hydrochloride, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ERIVEDGE (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (alfatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixapilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprorelin acetate), LUPRON DEPOT (leuprorelin acetate), LUPRON DEPOT-3 MONTH (leuprorelin acetate), LUPRON DEPOT-4 MONTH (leuprorelin acetate), LUPRON DEPOT-PED (leuprorelin acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), Mitoxantrone Hydrochloride, MITOZYTREX (mitomycin-c), MOZOBIL (plerixafor), MUSTARGEN (mechlorethamine hydrochloride), MUTAMYCIN (mitomycin-c), MYLOSAR (azacitidine), NAVELBINE (vinorelbine tartrate), NEOSAR (cyclophosphamide), NEXAVAR (sorafenib tosylate), NOLVADEX (tamoxifen citrate), NOLVADEX (tamoxifen citrate), OFF, PAD, PARAPLAT (carboplatin), PARAPLATIN (carboplati), PEG-INTRON (peginterferon alfa-2b), Pemetrexed Disodium, PERJETA (pertuzumab), PLATINOL (cisplatin), PLATINOL-AQ (cisplatin), POMALYST (pomalidomide), Prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib) SUTENT (sunitinib malate), SYLATRON (peginterferon alfa-2b), SYLVANT (cetuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprorelin acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate) or combinations thereof.

In one embodiment, the additional pharmaceutical agent is an antiviral agent. In one embodiment, the additional pharmaceutical agent is selected from epigenetic or transcriptional modulators (e.g., DNA methyltransferase inhibitors, histone deacetylase inhibitors (HDAC inhibitors), lysine methyltransferase inhibitors), anti-mitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In one embodiment, compounds or pharmaceutical compositions of the present disclosure may be administered in combination with anti-cancer therapy including, but not limited to, surgery, radiation therapy, transplantation (e.g., stem cell transplantation, bone marrow transplantation), immunotherapy and chemotherapy.

EXAMPLES

The following examples are provided to offer a complete disclosure and description of how to implement, prepare and evaluate the methods and compounds claimed herein for those skilled in the art. These examples are illustrative only and should not be construed as limiting the scope of the invention in any way.

The preparation scheme of the compounds of disclosed herein is shown, for example, in Scheme 1.

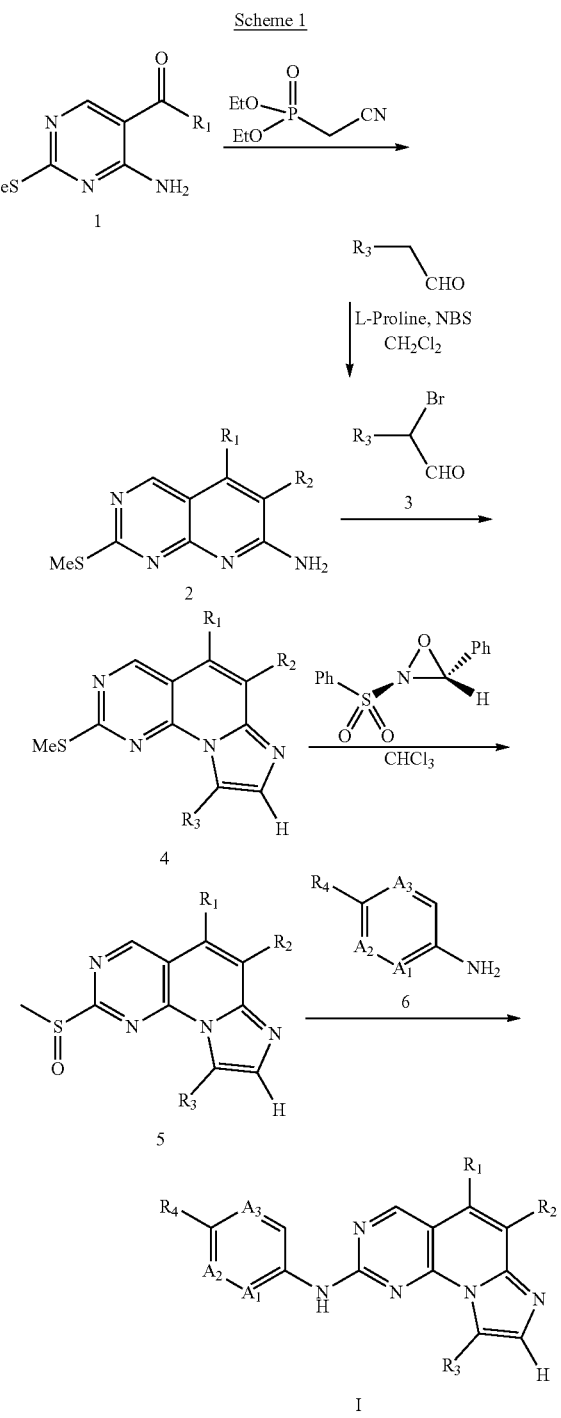

The compound of general formula I can be prepared according to the general reaction scheme above. First, the compound (1) is reacted with diethyl (cyanomethyl) phosphonate to give the pyrido[2,3-d]pyrimidine intermediate (2). Then, the compound (2) is reacted with freshly prepared alpha-bromo aldehyde (3) to afford imidazo[1',2':1,6]pyrido[2,3-d]pyrimidine intermediate (4) (the alpha-bromo aldehyde is prepared by the bromination reaction on the alpha-position of the carbonyl of the alpha-methylene aldehyde with N-bromosuccinimide in the presence of the catalyst L-proline). The methylthio group of the intermediate (4) is oxidized by Davis oxidant to get methylsulfinyl intermediate (5). The compound (5) is coupled with amine (6) to afford the compound of formula (I).

Example 1

9-Isopropyl-N-(5-(piperazin-1-yl)pyridin-2-yl)imidazo[1',2':1,6]pyrido[2,3-d]pyrimidin-2-amine hydrochloride (I-1)

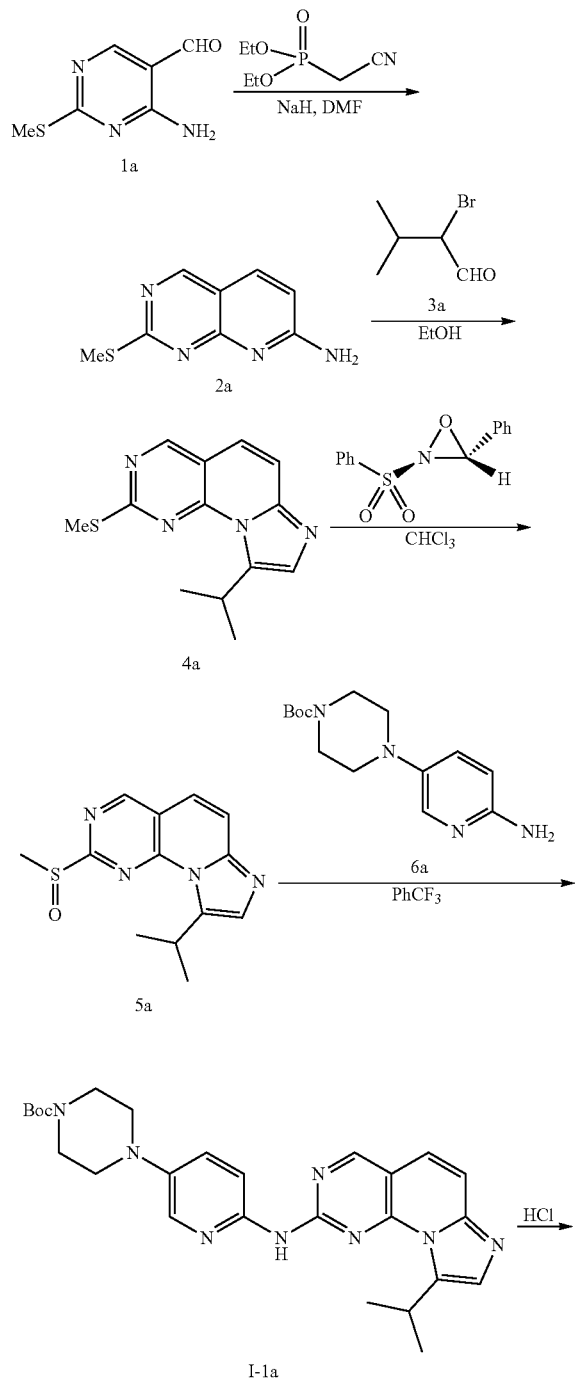

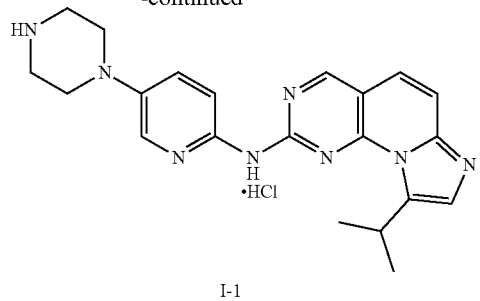

2-Methylthiopyrido[2,3-d]pyrimidin-7-amine (2a)

Under nitrogen protection, sodium hydride (60%, 12.0 g, 301 mmol) was suspended in N,N-dimethylformamide (200 mL). In an ice-water bath, diethyl cyanomethylphosphonate (53.1 g, 300 mmol) was added to the reaction solution dropwise, and the reaction was stirred at room temperature for 20 minutes. In the ice-water bath, 4-amino-2-methylthiopyrimidin-5-formaldehyde (1a, 16.9 g, 100 mmol) was added to the reaction solution, and the mixture was stirred overnight at room temperature. The reaction was quenched with saturated ammonium chloride aqueous solution (200 mL), and a white solid was precipitated out from the reaction solution. After filtration, the filter residue was washed with water (100 mL) and methyl tert-butyl ether (100 mL), and dried in vacuum to give the title compound 2a (12.0 g, 62.5%). $^1$H NMR (400 MHz, DMSO-$d_6$, ppm): δ 8.80 (s, 1H), 7.92 (d, J=8.8 Hz, 1H), 7.44 (br, 2H), 6.74 (d, J=8.8 Hz, 1H), 2.52 (s, 3H).

2-Bromo-3-methyl butyraldehyde (3a)

3-Methylbutyraldehyde (10 g, 116.3 mmol) was dissolved in dichloromethane (60 mL), and L-proline (1.34 g, 11.6 mmol) was added. N-bromosuccinimide (24.8 g, 139.3 mmol) was added to the reaction solution in an ice-water bath, and the mixture was warmed to room temperature and stirred for 2 hours. After filtration, the filtrate was concentrated, and purified by flash silica gel column chromatography (petroleum ether:ethyl acetate=5:1) to give the 2-bromo-3-methyl butyraldehyde (3a, 10 g, 52%) as a reddish-brown oily liquid. LC-MS (ESI), $C_5H_{10}BrO$ [M+H]$^+$:m/z=165.0, 167.1.

9-Isopropyl-2-(methylthio)imidazo[1',2':1,6]pyrido [2,3-d]pyrimidine (4a)

2a (10 g, 52.1 mmol) and freshly prepared 3a (9.4 g, 57.3 mmol) were dissolved in ethanol (100 mL), and the reaction solution was heated to reflux for 2 hours. The reaction solution was concentrated and diluted with water (200 mL), and the pH of the reaction solution was adjusted to around 8 with saturated sodium bicarbonate aqueous solution. The resulting solution was extracted with ethyl acetate three times, and the organic phases were combined. After being dried and concentrated, the combined organic phase was purified by column chromatography to give the title compound 4a (5.2 g, 38.6%) as a light brown solid. $^1$H NMR (300 MHz, DMSO-$d_6$, ppm): δ 9.24 (s, 1H), 7.65-7.54 (m, 2H), 7.49 (s, 1H), 4.38-4.29 (m, 1H), 2.66 (s, 3H), 1.41 (d, J=6.8 Hz, 6H); LC-MS (ESI), for $C_{13}H_{15}N_4S$[M+H]$^+$:m/z=259.

9-Isopropyl-2-(methylsulfinyl)imidazo[1',2':1,6]pyrido[2,3-d]pyrimidine (5a)

4a (4.5 g, 17.4 mmol) was dissolved in chloroform (40 mL), and 2-phenylsulfonyl-3-phenyloxaziridine (5.46 g, 20.9 mmol) was added. The resulting solution was stirred at room temperature for 18 hours. The reaction solution was concentrated, and the residue was purified by flash silica gel column chromatography to give the title compound 5a (4.05 g, 85%) as a white solid, $^1$H NMR (400 MHz, CDCl$_3$, ppm): δ 9.32 (s, 1H), 7.75 (d, J=9.2 Hz, 1H), 7.55 (s, 1H), 7.50 (d, J=9.2 Hz, 1H), 4.37-4.30 (m, 1H), 3.05 (s, 3H), 1.49-1.45 (m, 6H).

Tert-butyl 4-(6((9-isopropylimidazo[1',2':1,6]pyrido[2,3-d]pyrimidin-2-yl)amino)pyridin-3-yl)piperazin-1-carboxylate (I-1a)

5a (82.2 mg, 0.3 mmol) and tert-butyl 4-(6-aminopyridin-3-yl)piperazin-1-carboxylate 6a (83.4 mg, 0.3 mmol) were suspended in trifluorotoluene (0.6 mL), and the resulting solution was vacuumed and purged with argon for three times, and heated to 75° C. for 21 hours. A small amount of ethyl acetate was added to the reaction solution after it was cooled to room temperature. After stirring for about 2 hours, a red-brown solid was precipitated out from the reaction solution. After filtration, the filter residue was purified by flash column chromatography to give the title compound I-1a (22.3 mg, 15.2%) as an orange powder. $^1$H NMR (400 MHz, CDCl$_3$, ppm): δ 8.91 (s, 1H), 8.18 (d, J=8.8 Hz, 1H), 8.05 (s, 2H), 7.39-7.29 (m, 4H), 4.39-4.32 (m, 1H), 3.63 (t, J=2.4 Hz, 4H), 3.13 (t, J=16 Hz, 4H), 1.49 (s, 9H), 1.42 (d, J=6.4 Hz, 6H).

9-Isopropyl-N-(5-(piperazin-1-yl)pyridin-2-yl)imidazo[1',2':1,6]pyrido[2,3-d]pyrimidin-2-amine hydrochloride (I-1)

I-1a (16.2 mg, 0.0332 mmol) was dissolved in dichloromethane/methanol (1:1, 2 mL), and hydrogen chloride (4M, 1,4-dioxane solution, 0.83 mL) was added. After stirring at room temperature for 3 hours, the solvent was removed with a rotary evaporator under reduced pressure. The resulting crude product was stirred in ethyl acetate for 1 hour, and filtered to give the title compound I-1 (14 m, 99%) as an orange powder. $^1$H NMR (400 MHz, D$_2$O, ppm): δ9.52 (s, 1H), 8.27-8.19 (m, 2H), 7.98 (s, 1H), 7.79-7.67 (m, 3H), 4.40-4.33 (m, 1H), 3.61-3.51 (m, 8H), 1.45 (d, J=6.0 Hz, 6H).

Example 2

9-Isopropyl-N-(5-(4-methylpiperazin-1-yl)pyridin-2-yl)imidazo[1',2':1,6]pyrido[2,3-d]pyrimidin-2-amine (I-2)

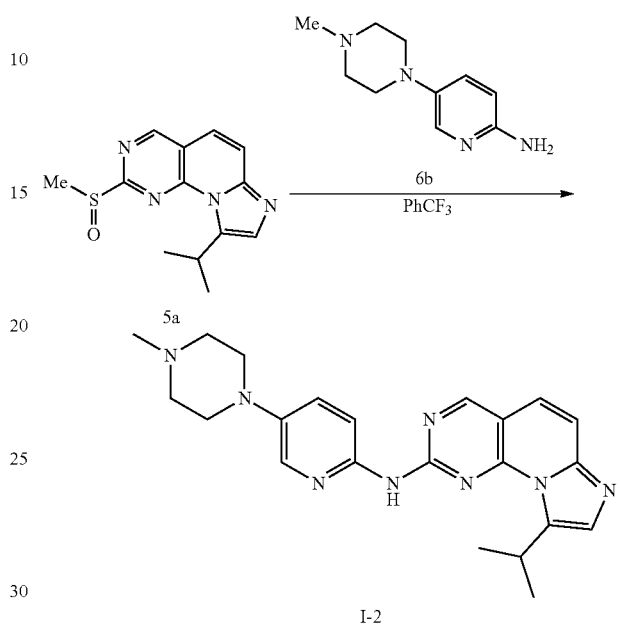

5a (63 mg, 0.23 mmol) and 5-(4-methylpiperazin-1-yl)pyridin-2-amine 6b (44.2 mg, 0.23 mmol) were suspended in trifluorotoluene (0.5 mL), and the resulting solution was vacuumed and purged with argon for three times, and heated to 75° C. for 21 hours. A small amount of ethyl acetate was added to the reaction solution after it was cooled to room temperature. After stirring for about 2 hours, a red-brown solid was precipitated out from the reaction solution. After filtration, the filter residue was purified by flash column chromatography to give the title compound I-2 (19.4 mg, 21%) as a orange powder. $^1$H NMR (400 MHz, chloroform-d, ppm) δ 8.90 (s, 1H), 8.14 (d, J=9.1 Hz, 1H), 8.05 (d, J=2.9 Hz, 1H), 8.01 (s, 1H), 7.40 (s, 1H), 7.36 (dd, J=9.0, 3.0 Hz, 1H), 7.30 (d, J=9.1 Hz, 1H), 4.39-4.30 (m, 1H), 3.25-3.20 (m, 4H), 2.64-2.60 (m, 4H), 2.38 (s, 3H), 1.41 (d, J=6.8 Hz, 6H).

TABLE 1

| Examples I-3 to I-30 | |
|---|---|
| Side chain | Product |
| 6c | I-3 |

TABLE 1-continued

Examples I-3 to I-30

| Side chain | | Product | |
|---|---|---|---|
| (structure) | 6d | (structure) | I-4 |
| (structure) | 6e | (structure) | I-5 |
| (structure) | 6f | (structure) | I-6 |
| (structure) | 6g | (structure) | I-7 |
| (structure) | 6h | (structure) ·HCl | I-8 |

TABLE 1-continued
Examples I-3 to I-30
| Side chain | | Product | |
|---|---|---|---|
| 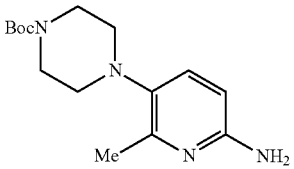 | 6i | 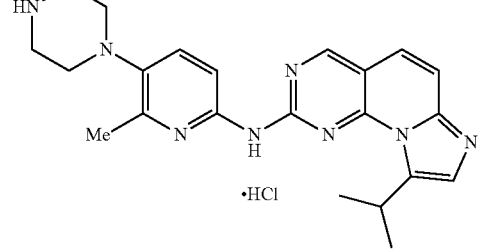 | I-9 |
| 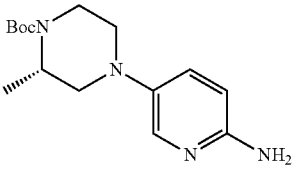 | 6j | 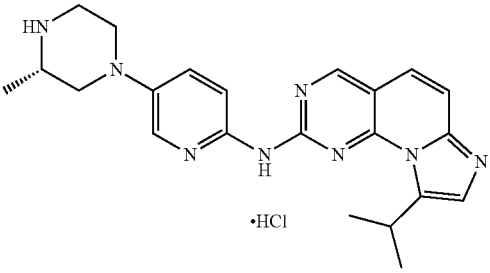 [SMILES: CC(C)c1cnc2ccc3cnc(Nc4ccc(N5CCN[C@@H](C)C5)cn4)nc3n12 ; Cl] | I-10 |
| 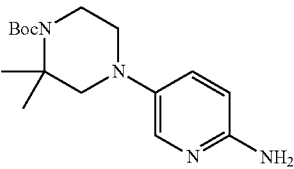 | 6k | 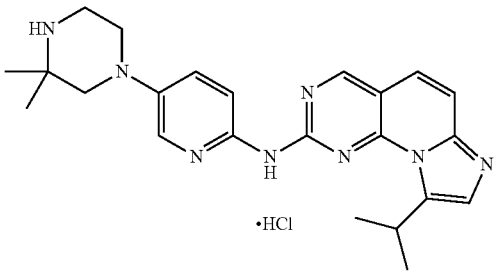 [SMILES: CC(C)c1cnc2ccc3cnc(Nc4ccc(N5CCNC(C)(C)C5)cn4)nc3n12 ; Cl] | I-11 |
| 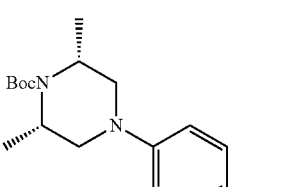 | 6l | 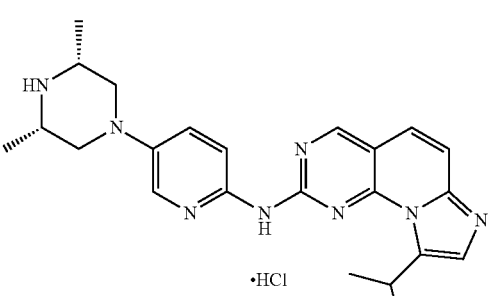 | I-12 |
| 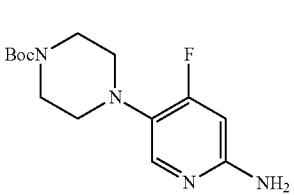 | 6m | 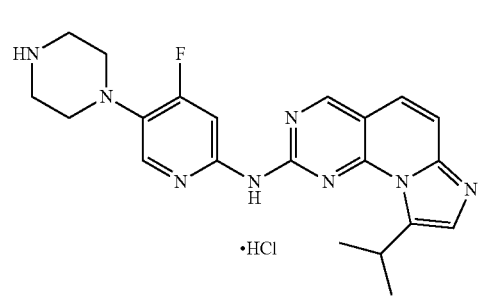 [SMILES: CC(C)c1cnc2ccc3cnc(Nc4cc(F)c(N5CCNCC5)cn4)nc3n12 ; Cl] | I-13 |

TABLE 1-continued
Examples I-3 to I-30
| Side chain | | Product | |
|---|---|---|---|
| 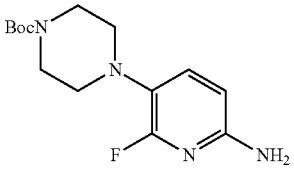 | 6n | 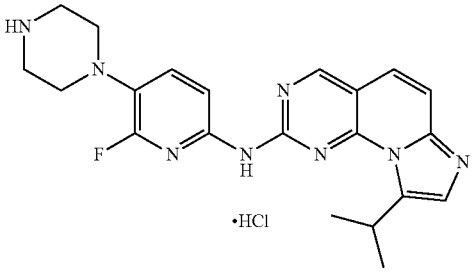 [SMILES: CC(C)c1cnc2ccc3cnc(Nc4ccc(N5CCNCC5)c(F)n4)nc3n12 ; Cl] ·HCl | I-14 |
| 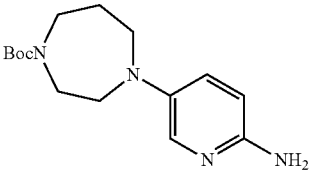 | 6o | 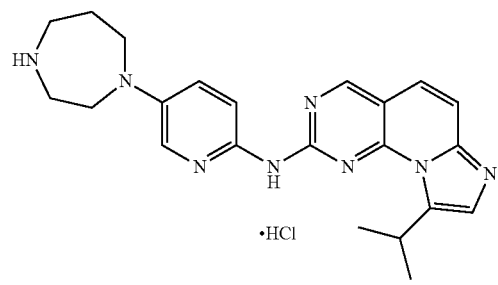 [SMILES: CC(C)c1cnc2ccc3cnc(Nc4ccc(N5CCCNCC5)cn4)nc3n12 ; Cl] ·HCl | I-15 |
| 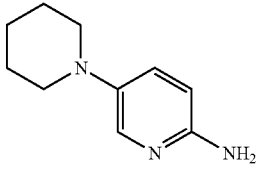 | 6p | 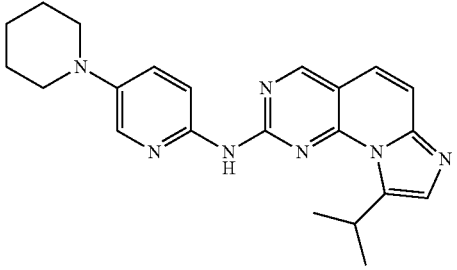 [SMILES: CC(C)c1cnc2ccc3cnc(Nc4ccc(N5CCCCC5)cn4)nc3n12] | I-16 |
| 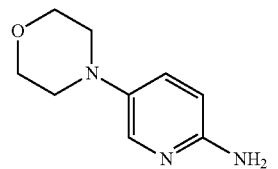 | 6q | 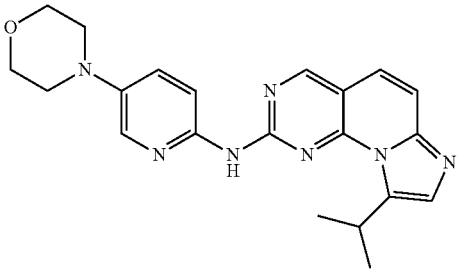 [SMILES: CC(C)c1cnc2ccc3cnc(Nc4ccc(N5CCOCC5)cn4)nc3n12] | I-17 |
| 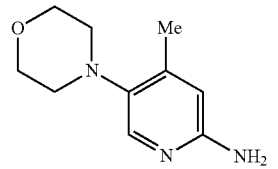 | 6r | 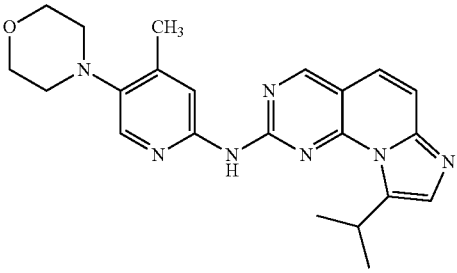 [SMILES: Cc1cc(Nc2ncc3ccc4ncc(C(C)C)n4c3n2)ncc1N1CCOCC1] | I-18 |

TABLE 1-continued
Examples I-3 to I-30
| Side chain | | Product | |
|---|---|---|---|
| 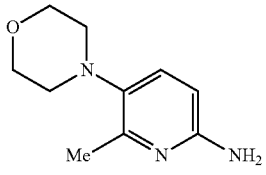 | 6s | 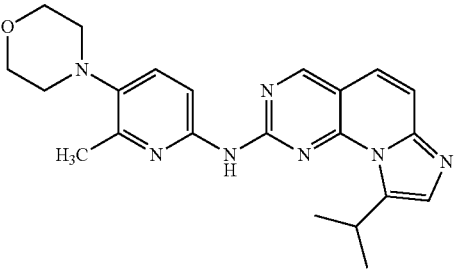 [SMILES: Cc1nc(Nc2ncc3ccc4ncc(C(C)C)n4c3n2)ccc1N1CCOCC1] | I-19 |
| 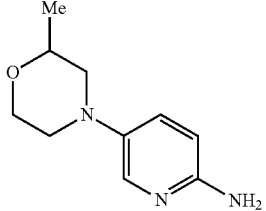 | 6t | 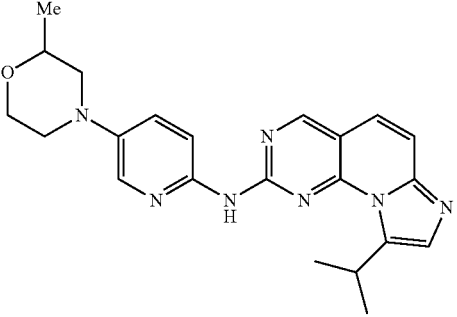 [SMILES: CC1CN(c2ccc(Nc3ncc4ccc5ncc(C(C)C)n5c4n3)nc2)CCO1] | I-20 |
| 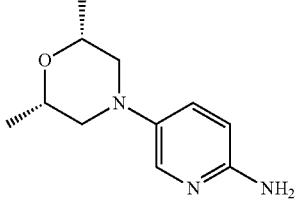 | 6u | 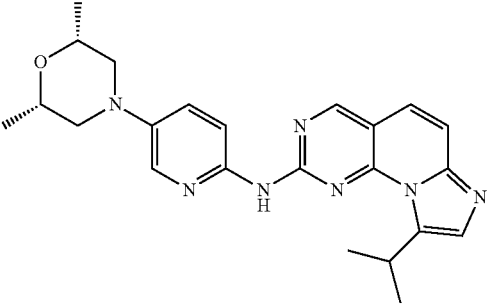 | I-21 |
| 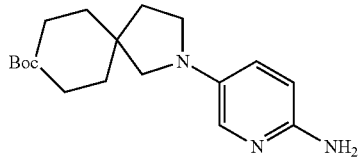 | 6v | 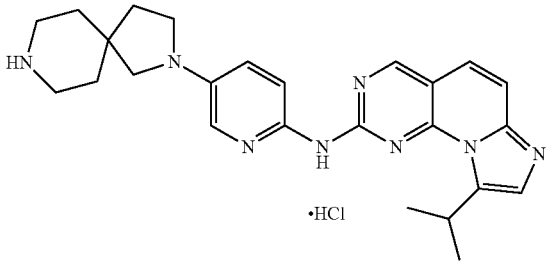 [SMILES: CC(C)c1cnc2ccc3cnc(Nc4ccc(N5CCC6(CCNCC6)C5)cn4)nc3n12 ; Cl]
·HCl | I-22 |
| 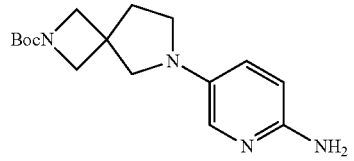 | 6w | 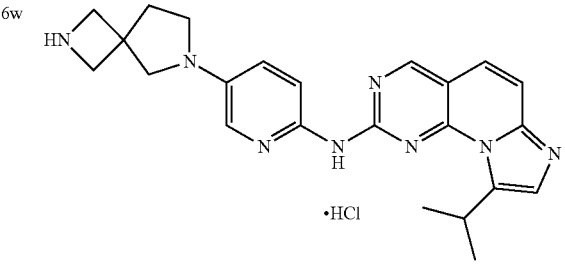
·HCl | I-23 |

TABLE 1-continued

Examples I-3 to I-30

| Side chain | | Product | |
|---|---|---|---|
| [structure] | 6x | [structure] •HCl | I-24 |
| [structure] | 6y | [structure] •HCl | I-25 |
| [structure] | 6z | [structure] | I-26 |
| [structure] | 6za | [structure] •HCl | I-27 |
| [structure] | 6zb | [structure] | I-28 |

TABLE 1-continued

Examples I-3 to I-30

| Side chain | | Product | |
|---|---|---|---|
| (structure with N-methylpiperidinyloxy, OMe, aniline) | 6zc | (product structure) | I-29 |
| (2-methoxyquinolin-6-amine) | 6zd | (product structure) | I-30 |

Referring to the synthetic method of I-1 in Example 1, 5a (60 mg, 0.219 mmol) and 6 (0.438 mmol, 2 equiv.) were used to prepare compounds I-8 (15.3 mg, 35.0 μmol, 16%), I-9 (21.1 mg, 48.2 μmol, 22%), I-10 (24.9 mg, 56.9 μmol, 26%), I-11 (70.2 mg, 39.4 μmol, 18%), I-12 (30.7 mg, 67.9 μmol, 31%), I-13 (13.6 mg, 30.7 μmol, 14%), I-14 (25.2 mg, 56.9 μmol, 26%), I-15 (22.1 mg, 50.4 μmol, 23%), I-22 (18.8 mg, 39.4 μmol, 18%), I-23 (23.7 mg, 52.6 μmol, 24%), I-24 (20.1 mg, 46.0 μmol, 21%), I-25 (16.2 mg, 35.0 μmol, 16%), I-26 (19.3 mg, 41.6 μmol, 19%) and I-27 (12.6 mg, 28.5 μmol, 13%).

I-8 $^1$H NMR (400 MHz, deuterium oxide-$d_2$, ppm) δ 9.52 (s, 1H), 8.26 (d, J=9.4 Hz, 1H), 8.09 (s, 1H), 7.85-7.70 (m, 2H), 7.60 (s, 1H), 4.46-4.38 (m, 1H), 3.65-3.20 (m, 8H), 2.60 (s, 3H), 1.45 (d, J=6.1 Hz, 6H).

I-9a $^1$H NMR (400 MHz, chloroform-d, ppm) δ 8.91 (s, 1H), 8.11 (d, J=8.7 Hz, 1H), 7.95 (s, 1H), 7.39 (dd, J=12.4, 8.7 Hz, 4H), 7.30 (d, J=9.2 Hz, 1H), 4.36 (p, J=6.8 Hz, 1H), 3.60 (t, J=4.9 Hz, 4H), 2.86 (t, J=5.0 Hz, 4H), 2.52 (s, 3H), 1.50 (s, 9H), 1.42 (d, J=6.8 Hz, 6H).

I-9 LC-MS (ESI), $C_{22}H_{27}N_8[M+H]^+$:m/z=403.1.

I-10 $^1$H NMR (400 MHz, chloroform-d, ppm) δ 8.90 (s, 1H), 8.17 (d, J=9.0 Hz, 1H), 8.02 (d, J=2.9 Hz, 1H), 7.97 (s, 1H), 7.40 (s, 1H), 7.39-7.27 (m, 3H), 4.45-4.29 (m, 2H), 4.00 (d, J=13.2 Hz, 1H), 3.46 (d, J=11.2 Hz, 1H), 3.36-3.20 (m, 2H), 2.97 (dd, J=11.8, 3.9 Hz, 1H), 2.79 (td, J=11.7, 3.6 Hz, 1H), 1.50 (s, 9H), 1.42 (d, J=6.8 Hz, 6H), 1.35 (d, J=6.8 Hz, 3H).

I-11a $^1$H NMR (400 MHz, chloroform-d, ppm) δ 8.88 (s, 1H), 8.09 (d, J=9.0 Hz, 1H), 7.93-7.86 (m, 2H), 7.38 (d, J=0.9 Hz, 1H), 7.35 (d, J=9.2 Hz, 1H), 7.28 (d, J=9.3 Hz, 1H), 7.15 (dd, J=9.1, 3.1 Hz, 1H), 4.35 (p, J=6.7 Hz, 1H), 3.82 (dd, J=6.2, 5.0 Hz, 2H), 3.40 (t, J=5.6 Hz, 2H), 3.29 (s, 2H), 1.51 (s, 9H), 1.46 (s, 6H), 1.41 (d, J=6.8 Hz, 6H).

I-11 LC-MS (ESI), $C_{23}H_{29}N_8[M+H]^+$:m/z 417.3.

I-12 $^1$H NMR (400 MHz, chloroform-d, ppm) δ 8.91 (s, 1H), 8.17 (d, J=9.0 Hz, 1H), 8.05 (d, J=3.1 Hz, 2H), 7.39 (d, J=0.9 Hz, 1H), 7.38-7.32 (m, 2H), 7.29 (d, J=9.3 Hz, 1H), 4.40-4.32 (m, 1H), 4.32-4.24 (m, 2H), 3.32 (d, J=11.8 Hz, 2H), 2.94 (dd, J=11.8, 4.4 Hz, 2H), 1.50 (s, 9H), 1.43 (s, 3H), 1.41 (s, 3H), 1.41 (s, 3H), 1.39 (s, 3H).

I-13 $^1$H NMR (400 MHz, deuterium oxide-$d_2$, ppm) δ 9.51 (s, 1H), 8.49 (d, J=9.1 Hz, 1H), 8.27 (d, J=9.4 Hz, 1H), 7.84-7.72 (m, 2H), 7.12 (s, 1H), 4.45-4.37 (m, 1H), 3.82 (q, J=5.6 Hz, 4H), 3.66-3.46 (m, 4H), 1.46 (d, J=6.7 Hz, 6H).

I-14 LC-MS (ESI), $C_{21}H_{24}FN_8[M+H]^+$:m/z=407.2.

I-15a $^1$H NMR (400 MHz, chloroform-d, ppm) δ 8.88 (s, 1H), 8.03 (d, J=13.4 Hz, 2H), 7.89 (s, 1H), 7.46-7.30 (m, 2H), 7.29 (s, 1H), 7.12 (dd, J=9.0, 2.3 Hz, 1H), 4.35 (p, J=6.9 Hz, 1H), 3.59 (dd, J=17.3, 6.5 Hz, 5H), 3.36 (t, J=5.9 Hz, 1H), 3.27 (t, J=6.0 Hz, 1H), 2.00 (dt, J=12.5, 5.9 Hz, 2H), 1.51-1.33 (m, 13H).

I-15 LC-MS (ESI), $C_{22}H_{27}N_8[M+H]^+$:m/z=403.1.
I-22 LC-MS (ESI), $C_{25}H_{31}N_8[M+H]^+$:m/z=443.3.
I-23 LC-MS (ESI), $C_{23}H_{27}N_8[M+H]^+$:m/z=415.2.
I-24 LC-MS (ESI), $C_{22}H_{25}N_8[M+H]^+$:m/z=401.3.

I-25 $^1$H NMR (400 MHz, chloroform-d ppm) δ 8.90 (s, 1H), 8.15 (d, J=9.0 Hz, 1H), 8.04 (d, J=2.8 Hz, 1H), 7.95 (s, 1H), 7.39 (d, J=1.0 Hz, 1H), 7.38-7.34 (m, 2H), 7.29 (d, J=9.3 Hz, 1H), 4.40-4.30 (m, 1H), 3.70 (s, 4H), 3.12 (dd, J=6.7, 4.4 Hz, 4H), 1.96-1.90 (m, 4H), 1.46 (s, 9H), 1.42 (d, J=6.8 Hz, 6H).

I-26 LC-MS (ESI), $C_{24}H_{29}N_8[M+H]^+$:m/z=429.3.
I-27 LC-MS (ESI), $C_{22}H_{25}FN_7[M+H]^+$:m/z=406.2.

Referring to the synthetic method of I-2 in Example 2, 5a (60 mg, 0.219 mmol) and 6 (0.438 mmol, 2 equiv.) were used to prepare compounds I-3 (16.4 mg, 39.4 μmol, 18%), I-4 (17.3 mg, 41.6 μmol, 19%), I-5 (23.7 mg, 56.9 μmol, 26%), I-6 (29.2 mg, 67.9 μmol, 31%), I-7 (20.7 mg, 48.2 μmol, 22%), I-16 (9.3 mg, 24.1 μmol, 11%), I-17 (17.9 mg, 46.0 μmol, 21%), I-18 (19.4 mg, 48.2 μmol, 13%), I-19 (16.8 mg, 41.6 μmol, 19%), I-20 (15.0 mg, 37.2 μmol, 17%), I-21 (23.7 mg, 56.9 μmol, 26%), I-28 (5.5 mg, 13.1 μmol, 6%), I-29 (8.9 mg, 19.7 μmol, 9%), I-30 (9.3 mg, 24.1 μmol, 11%).

I-3 $^1$H NMR (400 MHz, chloroform-d, ppm) δ 8.92 (s, 1H), 8.05 (d, J=3.8 Hz, 3H), 7.41 (s, 1H), 7.38 (d, J=9.3 Hz, 1H), 7.31 (d, J=9.3 Hz, 1H), 4.35 (p, J=6.8 Hz, 1H), 3.04 (t, J=4.8 Hz, 4H), 2.64 (m, 4H), 2.41 (d, J=0.8 Hz, 6H), 1.41 (d, J=6.7 Hz, 7H).

I-4 ¹H NMR (400 MHz, chloroform-d, ppm) δ 8.90 (s, 1H), 8.09 (d, J=8.6 Hz, 1H), 7.91 (s, 1H), 7.45 (d, J=8.7 Hz, 1H), 7.39 (d, J=1.0 Hz, 1H), 7.36 (d, J=9.3 Hz, 1H), 7.29 (d, J=9.2 Hz, 1H), 4.39-4.32 (m, 1H), 2.99 (t, J=4.8 Hz, 4H), 2.68 (m, 4H), 2.50 (s, 3H), 2.43 (s, 3H), 1.41 (d, J=6.8 Hz, 6H).

I-5 ¹H NMR (400 MHz, chloroform-d, ppm) δ 8.90 (s, 1H), 8.16 (d, J=9.0 Hz, 1H), 8.05 (d, J=2.9 Hz, 1H), 7.99 (s, 1H), 7.39 (d, J=0.9 Hz, 1H), 7.39-7.34 (m, 2H), 7.29 (d, J=9.3 Hz, 1H), 4.36 (dt, J=12.7, 6.4 Hz, 1H), 3.29-3.22 (m, 4H), 2.69 (t, J=5.1 Hz, 4H), 2.53 (q, J=7.2 Hz, 2H), 1.42 (d, J=6.8 Hz, 6H), 1.16 (t, J=7.2 Hz, 3H).

I-6 ¹H NMR (400 MHz, chloroform-d, ppm) δ 8.92 (s, 1H), 8.13-8.02 (m, 3H), 7.41 (d, J=1.0 Hz, 1H), 7.38 (d, J=9.2 Hz, 1H), 7.31 (d, J=9.2 Hz, 1H), 4.35 (p, J=6.6 Hz, 1H), 3.08 (brs, 4H), 2.71 (m, 4H), 2.58 (d, J=7.7 Hz, 2H), 2.41 (s, 3H), 1.41 (d, J=6.8 Hz, 6H), 1.19 (t, J=7.2 Hz, 3H).

I-7 ¹H NMR (400 MHz, chloroform-d, ppm) δ 8.90 (s, 1H), 8.09 (d, J=8.8 Hz, 1H), 7.98 (s, 1H), 7.47 (d, J=8.7 Hz, 1H), 7.39 (d, J=0.9 Hz, 1H), 7.37 (d, J=9.3 Hz, 1H), 7.29 (d, J=9.3 Hz, 1H), 4.34 (td, J=13.1, 12.6, 6.7 Hz, 1H), 3.04 (s, 4H), 2.77 (brs, 4H), 2.64 (d, J=7.5 Hz, 2H), 2.50 (s, 3H), 1.41 (d, J=6.8 Hz, 6H), 1.28-1.21 (m, 3H).

I-16 ¹H NMR (400 MHz, chloroform-d, ppm) δ 8.89 (s, 1H), 8.12 (d, J=9.0 Hz, 1H), 8.08-8.03 (m, 1H), 7.97 (s, 1H), 7.39 (d, J=0.9 Hz, 1H), 7.38-7.34 (m, 2H), 7.29 (d, J=9.3 Hz, 1H), 4.41-4.30 (m, 1H), 3.21-3.11 (m, 4H), 1.76 (p, J=5.7 Hz, 4H), 1.62 (d, J=10.7 Hz, 6H), 1.41 (d, J=6.8 Hz, 6H).

I-17 ¹H NMR (400 MHz, chloroform-d) δ 8.91 (s, 1H), 8.18 (d, J=8.8 Hz, 1H), 8.07 (d, J=17.2 Hz, 2H), 7.34 (dt, J=20.1, 9.9 Hz, 4H), 4.41-4.30 (m, 1H), 4.01-3.81 (m, 4H), 3.29-3.10 (m, 4H), 1.42 (d, J=6.8 Hz, 6H).

I-18 ¹H NMR (400 MHz, chloroform-d/methanol-d₄=1:1, ppm) δ 8.95 (s, 1H), 7.96 (s, 1H), 7.92 (s, 1H), 7.46 (d, J=1.6 Hz, 1H), 7.41 (d, J=9.3 Hz, 1H), 7.31-7.28 (m, 1H), 4.29 (p, J=6.8 Hz, 1H), 3.90-3.80 (m, 4H), 2.97 (dd, J=5.6, 3.4 Hz, 4H), 2.40 (s, 3H), 1.34 (d, J=6.8 Hz, 6H).

I-19 ¹H NMR (400 MHz, chloroform-d, ppm) δ 8.91 (s, 1H), 8.11 (d, J=8.7 Hz, 1H), 7.93 (s, 1H), 7.44 (d, J=8.7 Hz, 1H), 7.39 (d, J=1.0 Hz, 1H), 7.37 (d, J=9.3 Hz, 1H), 7.30 (d, J=9.3 Hz, 1H), 4.41-4.31 (m, 1H), 3.91-3.86 (m, 4H), 2.96-2.90 (m, 4H), 2.52 (s, 3H), 1.42 (d, J=6.8 Hz, 6H).

I-20 ¹H NMR (400 MHz, chloroform-d, ppm) δ 8.90 (s, 1H), 8.17 (d, J=9.1 Hz, 1H), 8.10-7.98 (m, 2H), 7.44-7.27 (m, 4H), 4.36 (hept, J=6.6 Hz, 1H), 4.08-4.02 (m, 1H), 3.88-3.76 (m, 2H), 3.45-3.34 (m, 2H), 2.88 (td, J=11.6, 3.4 Hz, 1H), 2.55 (dd, J=11.5, 10.3 Hz, 1H), 1.42 (d, J=6:8 Hz, 6H), 1.28 (d, J=6.3 Hz, 3H).

I-21 ¹H NMR (400 MHz, chloroform-d, ppm) δ 8.90 (s, 1H), 8.16 (d, J=9.0 Hz, 1H), 8.06 (s, 1H), 8.03 (d, J=2.9 Hz, 1H), 7.39 (s, 1H), 7.38-7.31 (m, 2H), 7.29 (d, J=9.3 Hz, 1H), 4.36 (p, J=6.7 Hz, 1H), 3.85 (dtt, J=12.5, 6.2, 3.1 Hz, 2H), 3.46-3.36 (m, 2H), 2.52-2.42 (m, 2H), 1.42 (d, J=6.8 Hz, 6H), 1.29 (d, J=6.3 Hz, 6H).

I-28 ¹H NMR (400 MHz, chloroform-d, ppm) δ 8.91 (s, 1H), 7.55 (d, J=8.6 Hz, 1H), 7.48 (d, J=9.3 Hz, 1H), 7.26 (s, 1H), 7.20 (d, J=9.3 Hz, 1H), 6.75 (d, J=2.5 Hz, 1H), 6.65 (dd, J=8.6, 2.6 Hz, 1H), 4.29 (t, J=5.2 Hz, 2H), 3.24 (t, J=5.1 Hz, 2H), 2.71 (s, 6H), 1.16 (d, J=6.8 Hz, 6H).

I-29 LC-MS (ESI), C₂₅H₃₁N₆O, [M+H]⁺:m/z=447.1.

I-30 ¹H NMR (400 MHz, chloroform-d, ppm) δ 8.89 (s, 1H), 8.01 (d, J=2.4 Hz, 1H), 7.97 (d, J=8.8 Hz, 1H), 7.88 (d, J=8.9 Hz, 1H), 7.73 (dd, J=8.9, 2.5 Hz, 1H), 7.55 (s, 1H), 7.37 (d, J=6.2 Hz, 2H), 7.31 (d, J=9.3 Hz, 1H), 6.95 (d, J=8.8 Hz, 1H), 4.29 (p, J=6.8 Hz, 1H), 4.10 (s, 3H), 1.28 (d, J=5.2 Hz, 6H).

Preparation of Key Intermediate 9-cyclopentyl-2-(methylsulfinyl)imidazo[1',2':1,6]pyrido[2,3-d]pyrimidine (5b)

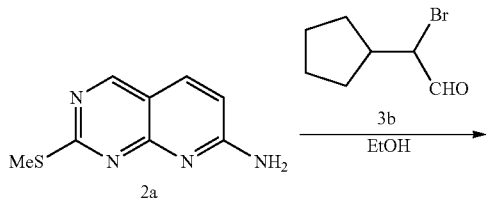

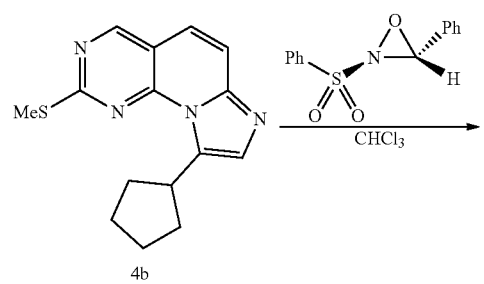

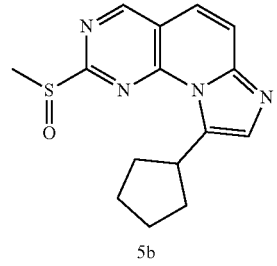

Referring to the synthetic method of 3a in Example 1, cyclopentyl acetaldehyde (3 g, 26.76 mmol) was used to prepare 2-bromo-2-cyclopentyl acetaldehyde (3b, 2.49 g, 13.11 mmol, 49%). LC-MS (ESI), C₇H₁₂BrO[M+H]⁺:m/z=191.0, 193.1.

Referring to the synthetic method of 4a in Example 1, 2a (2.50 g, 13.0 mmol) and freshly prepared 3b (2.49 g, 13.11 mmol) were used to prepare 9-cyclopentyl-2-(methylthio)imidazo[1',2':1,6]pyrido[2,3-d]pyrimidine (4b, 1.33 g, 4.68 mmol, 36%). ¹H NMR (400 MHz, chloroform-d, ppm): δ 8.92 (s, 1H), 7.50 (d, J=9.2 Hz, 1H), 7.45 (s, 1H), 7.32 (d, J=9.2 Hz, 1H), 4.43-4.36 (m, 1H), 2.67 (s, 3H), 2.33-2.26 (m, 2H), 1.91-1.82 (m, 2H), 1.78-1.68 (m, 4H).

Referring to the synthetic method of 5a in Example 1, 4b (1.3 g, 4.58 mmol) was used to prepare 9-cyclopentyl-2-(methylsulfinyl)imidazo[1',2':1,6]pyrido[2,3-d]pyrimidine (5b, 1.21 g, 88%). ¹H NMR (400 MHz, CDCl₃, ppm): δ 9.30 (s, 1H), 7.76 (d, J=9.6 Hz, 1H), 7.56 (s, 1H), 7.49 (d, J=9.2 Hz, 1H), 4.38-4.30 (m, 1H), 3.04 (s, 3H), 2.40-2.34 (m, 2H), 1.84-1.71 (m, 6H).

TABLE 2
Examples I-42 to I-46
| Side chain | Product |
|---|---|
| 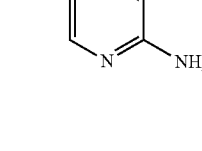 6a | 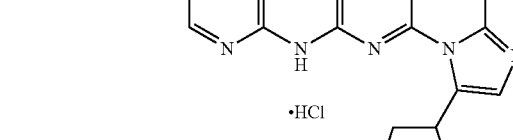 I-31 |
| 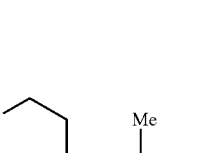 6f | 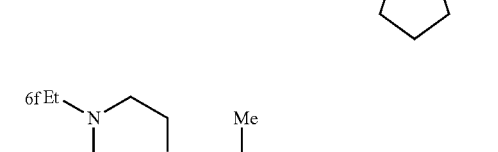 I-32 |
| 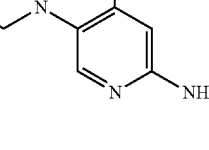 6h | 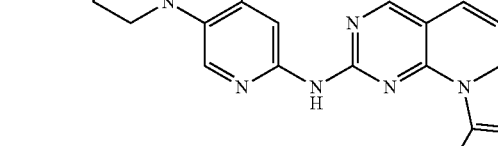 I-33 |
|  6i |  I-34 |

TABLE 2-continued

Examples I-42 to I-46

| Side chain | | Product | |
|---|---|---|---|
| (structure) | 6l | (structure) •HCl | I-35 |
| (structure) | 6m | (structure) •HCl | I-36 |
| (structure) | 6n | (structure) •HCl | I-37 |
| (structure) | 6r | (structure) | I-38 |

TABLE 2-continued

Examples I-42 to I-46

| Side chain | Product |
|---|---|
| 6u | I-39 |

Referring to the synthetic method of I-1 in Example 1, 5b (60 mg, 0.2 mmol) and 6 (0.4 mmol, 2 equiv.) were used to prepare compounds I-31 (13.5 mg, 30.0 μmol, 15%), I-33 (12.1 mg, 26.0 μmol, 13%), I-34 (15.8 mg, 34.0 μmol, 17%), I-35 (10.5 mg, 22.0 μmol, 11%), I-36 (21.5 mg, 46.0 μmol, 23%), I-37 (17.8 mg, 38.0 μmol, 19%).

I-31 $^1$H NMR (400 MHz, deuterium oxide-d$_2$, ppm) δ 9.50 (s, 1H), 8.26 (d, J=9.3 Hz, 1H), 8.20 (dd, J=9.6, 2.7 Hz, 1H), 8.03 (s, 1H), 7.80 (s, 1H), 7.74 (t, J=10.0 Hz, 2H), 4.37 (dt, J=14.2, 7.4 Hz, 1H), 3.72-3.56 (m, 4H), 3.56-3.41 (m, 4H), 2.36-2.19 (m, 2H), 1.91-1.58 (m, 6H).

I-33 $^1$H NMR (400 MHz, deuterium oxide-d$_2$, ppm) δ 9.49 (s, 1H), 8.24 (t, J=8.4 Hz, 2H), 7.78 (s, 1H), 7.74 (d, J=9.3 Hz, 1H), 7.65 (d, J=9.1 Hz, 1H), 4.32-4.23 (m, 1H), 3.51 (d, J=4.3 Hz, 4H), 3.40-3.24 (m, 4H), 2.77 (s, 3H), 2.24-2.13 (m, 2H), 1.82-1.53 (m, 6H).

I-34 $^1$H NMR (400 MHz, deuterium oxide-d$_2$, ppm) δ 9.48 (d, J=2.7 Hz, 1H), 8.28-8.22 (m, 1H), 8.19 (dd, J=9.0, 4.1 Hz, 1H), 7.78 (s, 1H), 7.74 (dd, J=9.3, 2.7 Hz, 1H), 7.64 (dd, J=8.9, 2.9 Hz, 1H), 3.59-3.45 (m, 4H), 3.33 (d, J=3.4 Hz, 3H), 2.76 (d, J=2.8 Hz, 3H), 1.82-1.49 (m, 6H).

I-35 $^1$H NMR (400 MHz, deuterium oxide-d$_2$, ppm) δ 9.46 (s, 2H), 8.23 (d, J=9.0 Hz, 1H), 8.17-8.11 (m, 1H), 8.06 (s, 1H), 7.78 (s, 1H), 7.71 (t, J=9.8 Hz, 2H), 4.36-4.28 (m, 1H), 3.98 (d, J=13.4 Hz, 2H), 3.67-3.56 (m, 2H), 2.96 (t, J=12.0 Hz, 2H), 2.27-2.15 (m, 2H), 1.85-1.57 (m, 6H), 1.43 (d, J=6.2 Hz, 6H).

I-36 $^1$H NMR (400 MHz, deuterium oxide-d$_2$, ppm) δ 9.49 (s, 1H) 8.45 (s, 1H), 8.25 (d, J=9.3 Hz, 1H), 7.91-7.64 (m, 2H), 7.15 (s, 1H), 4.41-4.26 (m, 1H), 3.85 (d, J=18.7 Hz, 4H), 3.58 (d, J=15.8 Hz, 4H), 2.41-2.17 (m, 2H), 2.00-1.44 (m, 6H).

I-37 LC-MS (ESI), $C_{23}H_{26}FN_8[M+H]^+$:m/z=433.1.

Referring to the synthetic method of I-2 in Example 2, 5b (60 mg, 0.2 mmol) and 6 (0.4 mmol, 2 equiv.) were used to prepare compounds I-32 (19.2 mg, 42.0 μmol, 21%), I-38 (18.9 mg, 44.0 μmol, 22%) and I-39 (11.5 mg, 26.0 μmol, 13%).

I-32 $^1$H NMR (400 MHz, chloroform-d, ppm) δ 8.92 (s, 1H), 8.06 (s, 1H), 8.02 (s, 2H), 7.41 (s, 1H), 7.37 (d, J=9.3 Hz, 1H), 7.30 (d, J=9.3 Hz, 1H), 4.30 (dt, J=14.7, 7.1 Hz, 3.05 (d, J=4.5 Hz, 4H), 2.85-2.59 (m, 4H), 2.59-2.50 (m, 2H), 2.39 (s, 3H), 2.25-2.15 (m, 2H), 1.80-1.62 (m, 8H), 1.17 (t, J=7.1 Hz, 3H).

I-38 $^1$H NMR (400 MHz, chloroform-d, ppm) δ 8.93 (s, 1H), 8.04 (s, 3H), 7.44-7.34 (m, 2H), 7.31 (d, J=9.3 Hz, 1H), 4.31 (p, J=7.4 Hz, 1H), 3.95-3.80 (m, 4H), 3.06-2.92 (m, 4H), 2.41 (s, 3H), 2.27-2.17 (m, 2H), 1.88-1.64 (m, 6H).

I-39 $^1$H NMR (400 MHz, chloroform-d, ppm) δ 8.90 (s, 1H), 8.10 (d, J=9.0 Hz, 1H), 8.03 (d, J=2.7 Hz, 1H), 7.93 (s, 1H) 7.40 (s, 1H), 7.38-7.27 (m, 3H), 4.34-4.25 (m, 1H), 3.85 (dtt, J=12.5, 6.2, 3.0 Hz, 2H), 3.44-3.34 (m, 2H), 2.52-2.41 (m, 2H), 2.23 (s, 2H), 1.82 (s, 2H), 1.67 (s, 4H), 1.29 (d, J=6.3 Hz, 6H).

Biological Examples

Potency determination of biochemical kinase inhibition test. Kinase activity test and IC50 determination. Firstly, 10 ng of recombinant CDK4/Cyclin D1 (Life Technologies PV4204) was diluted in kinase buffer (20 mM Tris pH 7.5, 10 mM MgCl$_2$, 0.01% NP-40, 2 mM DTT), and was incubated with inhibitors at the indicated concentration at room temperature for 30 minutes. The kinase reaction was initiated by adding 1 μg (1.5 μM) of recombinant retinoblastoma protein, 5 μM ATP and 10μ Ci γ-32P-ATP. The reaction was incubated at 30° C. for 20 minutes, and was terminated by adding 2×Laemmli sample buffer, heated at 95° C. for three minutes, and the resulting solution was dissolved with 12% acrylamide SDS-PAGE and autoradiographed. A densitometer (Bio-Rad) was used to quantify the corresponding phosphorylated substrate protein bands. The resulting density values were plotted as a function of the log drug concentration using Prism 4 Graphpad software, IC50 values were determined by plotting a non-linear regression curve with a variable slope.

The inhibitory activity of the compounds disclosed herein against CDK6/cyclin D1 was tested by a similar method.

Results of the enzyme inhibitory activity of the most representative compounds of the present disclosure are shown in the following table. The compounds were tested in a three-fold serial dilution from the starting concentration of 10 μM, over 10-fold of IC50. The control compound, staurosporine, was tested in a four-fold serial dilution from the starting concentration of 20 μM, over 10-fold of IC50. These reactions took place in the presence of 10 μM ATP.

| Compound No. | CDK4/Cydin D1 IC50 (nM) | CDK6/Cyelin D1 IC50 (nM) |
|---|---|---|
| Staurosporine | 4.06 | 10.8 |
| I-1 | 1-5 | <1 |
| I-2 | <1 | <1 |

-continued

| Compound No. | CDK4/Cydin D1 IC50 (nM) | CDK6/Cyelin D1 IC50 (nM) |
|---|---|---|
| I-3 | 5-10 | 5-10 |
| I-4 | 5-10 | 5-10 |
| I-5 | <1 | <1 |
| I-6 | 10-20 | 5-10 |
| I-7 | 5-10 | 5-10 |
| I-8 | 1-5 | <1 |
| I-9 | 5-10 | <1 |
| I-10 | 5-10 | 5-10 |
| I-11 | 5-10 | 5-10 |
| I-12 | 5-10 | 5-10 |
| I-13 | 10-20 | 5-10 |
| I-14 | 20-50 | 10-20 |
| I-15 | 20-50 | 20-50 |
| I-16 | 20-50 | 20-50 |
| I-17 | 5-10 | <1 |
| I-18 | 10-20 | 1-5 |
| I-19 | 5-10 | 5-10 |
| I-20 | 5-10 | 5-10 |
| I-21 | 20-50 | 10-20 |
| I-22 | 20-50 | 20-50 |
| I-23 | 20-50 | 20-50 |
| I-24 | 20-50 | 20-50 |
| I-25 | 20-50 | 20-50 |
| I-26 | 20-50 | 20-50 |
| I-27 | 50-100 | 50-100 |
| I-28 | 50-100 | 50-100 |
| I-29 | 50-100 | 50-100 |
| I-30 | 50-100 | 50-100 |
| I-31 | 1-5 | <1 |
| I-32 | 5-10 | 5-10 |
| I-33 | 5-10 | <1 |
| I-34 | 5-10 | <1 |
| I-35 | 5-10 | 5-10 |
| I-36 | 10-20 | 10-20 |
| I-37 | 5-10 | 5-10 |
| I-38 | 10-20 | 1-5 |
| I-39 | 20-50 | 10-20 |

It is worth noting that the compounds of the present disclosure also have selectivity between CDK6/cyclin D1 and CDK4/cyclin D1 in terms of their enzyme inhibitory activity. For example, the selectivity of compounds I9, I17, I33 and I34 for CDK6/cyclin D1 is more than 10 tunes of that for CDK4/cyclin D1. The selectivity of compounds I1, I8 and I31 for CDK6/cyclin D1 is more than 5 times of that for CDK4/cyclin D1. The selectivity of I18 and I38 for CDK6/cyclin D1 is about 4 times of that for CDK4/cyclin D1. The selectivity of compounds I6, I7, I13, I14, I21 and I39 for CDK6/cyclin D1 is 2-3 times of that for CDK4/cyclin D1.

In addition, the inhibitory activities of the compounds of the present disclosure against enzyme ABL1, FLT3 and PIM1 were also tested. It was found that the compounds of the present disclosure can effectively, inhibit ABL1, FLT3 and PIM1 simultaneously. For example, the IC50 value of inhibition against ABL1 is less than 100 nM, the IC50 value of inhibition against FLT3 is less than 20 nM and the IC50 value of inhibition against PIM1 is less than 100 nM, Preferably, the IC50 values of inhibition against FLT3 and PIM1 of the compounds I1, I8, I9, I17, I18, I31, I33, I34 and I38 are less than 5 nM and less than 50 nM, respectively.

While the present disclosure has been described in detail with reference to the specific preferred embodiments, it cannot be concluded that the specific embodiments of the present disclosure are limited to these descriptions. Those skilled in the art will appreciate that several simple deductions or substitutions may be made without departing from the spirit of the present disclosure, which should be regarded to be within the scope of the present disclosure.

The invention claimed is:
1. A compound of formula (I), or pharmaceutically acceptable salts, enantiomers, diastereomers, racemates, solvates, hydrates, polymorphs, or isotope variants thereof:

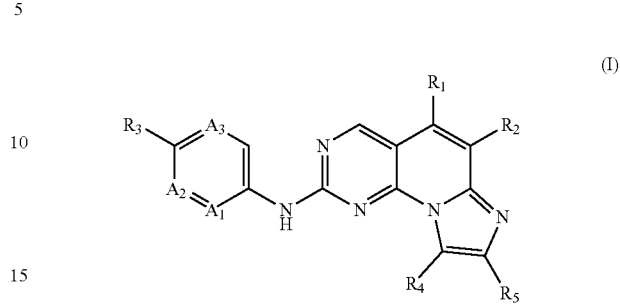

(I)

wherein:
$A_1$ is N;
$A_2$ is $CR_3$;
$A_3$ is $CR_3$;
$R_1$ is hydrogen;
$R_2$ is hydrogen;
$R_3$ is selected from hydrogen, halogen, —CN, —NO$_2$, —OR$_a$, —SR$_a$, —NR$_b$R$_c$, —O—C$_{1-6}$ alkylene-R$_6$, C$_{1-6}$ alkyl, C$_{1-6}$ haloalkyl, -L'-C$_{3-7}$ cycloalkyl, -L'-3- to 11-membered heterocyclyl, -L'-C$_{6-10}$ aryl or -L'-5- to 10-membered heteroaryl, said groups are optionally substituted with 1, 2, 3, 4 or 5 R$_6$ groups;
$R_4$ is selected from C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl;
$R_5$ is hydrogen;
$R_6$ is selected from hydrogen, —NH$_2$, —NHC$_{1-6}$ alkyl, —N(C$_{1-6}$ alkyl)$_2$, C$_{1-6}$ alkyl or C$_{1-6}$ haloalkyl;
or two R$_6$ groups on a same carbon atom are taken together to form oxo or thioxo;
wherein:
$R_4$ is optionally substituted with 1, 2 or 3 R' groups, wherein R' is independently selected from hydrogen, halogen, —CN, —NO$_2$, —OR$_a$, —SR$_a$, —NR$_b$R$_c$, —C(O)OR$_a$, —C(O)NR$_b$R$_c$, C$_{1-6}$ alkyl, C$_{1-6}$ haloalkyl, C$_{3-7}$ cycloalkyl, 3- to 7-membered heterocyclyl, C$_{6-10}$ aryl or 5- to 10-membered heteroaryl;
$R_a$ is independently selected from hydrogen, C$_{1-6}$ alkyl, C$_{2-6}$ alkenyl, C$_{2-6}$ alkynyl or C$_{1-6}$ haloalkyl;
$R_b$ and $R_c$ are independently selected from hydrogen, C$_{1-6}$ alkyl, C$_{2-6}$ alkenyl, C$_{2-6}$ alkynyl or C$_{1-6}$ haloalkyl; or $R_b$, $R_c$ and N atom are taken together to form a 3- to 7-membered heterocyclyl; and
L' is selected from a chemical bond or —O—.

2. A compound of formula (II), or pharmaceutically acceptable salts, enantiomers, diastereomers, racemates, solvates, hydrates, polymorphs, or isotope variants thereof:

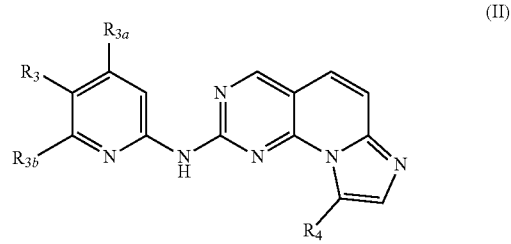

(II)

wherein:
R₃ is

[structure: piperazine with R₃c on N, NH*]

R₃ₐ, R₃ᵦ and R₃c are independently selected from hydrogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl, provided that at most one of R₃ₐ, R₃ᵦ and R₃c is not hydrogen; and R₄ is selected from $C_{1-6}$ alkyl, $C_{1-6}$ haloalkyl, $C_{3-7}$ cycloalkyl or 3- to 7-membered heterocyclyl.

3. The compound, or pharmaceutically acceptable salts, enantiomers, diastereomers, racemates, solvates, hydrates, polymorphs, or isotope variants thereof according to claim 2, wherein, R₃ is

[structure: piperazine with R₃c on N, NH*]

R₃ₐ, R₃ᵦ and R₃c are independently selected from hydrogen, $C_{1-6}$ alkyl or $C_{1-6}$ haloalkyl, provided that at most one of R₃ₐ, R₃ᵦ and R₃c is not hydrogen; and R₄ is selected from $C_{1-6}$ alkyl, $C_{1-6}$ haloalkyl, $C_{3-7}$ cycloalkyl or 3- to 7-membered heterocyclyl.

4. The compound, or pharmaceutically acceptable salts, enantiomers, diastereomers, racemates, solvates, hydrates, polymorphs, or isotope variants thereof according to claim 2, wherein, R₃ is

[structure: piperazine with R₃c on N, NH*]

R₃ₐ, R₃ᵦ and R₃c are independently selected from hydrogen or $C_{1-6}$ alkyl, provided that at most one of R₃ₐ, R₃ᵦ and R₃c is not hydrogen; and R₄ is selected from $C_{1-6}$ alkyl or $C_{3-7}$ cycloalkyl.

5. A compound of formula (II), or pharmaceutically acceptable salts, enantiomers, diastereomers, racemates, solvates, hydrates, polymorphs, or isotope variants thereof:

(II)

[chemical structure of formula (II) with substituents R₃ₐ, R₃ᵦ, R₃c, R₄]

wherein:
R₃ is selected from

[structures: piperazine with R₃c; piperazine with R₃d and R₃e; piperazine with R₃e and R₃f; morpholine-type with R₃d and O; thiomorpholine-type with R₃d and S]

R₃ₐ, R₃ᵦ, R₃c, R₃d, R₃e and R₃f are independently selected from hydrogen, halogen, —CN, —NO₂, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; and R₄ is selected from $C_{1-6}$ alkyl, $C_{1-6}$ haloalkyl, $C_{3-7}$ cycloalkyl or 3- to 7-membered heterocyclyl.

6. The compound, or pharmaceutically acceptable salts, enantiomers, diastereomers, racemates, solvates, hydrates, polymorphs, or isotope variants thereof according to claim 5, wherein, R₃ is selected from

[structures: piperazine with R₃c; piperazine with R₃d and R₃e; piperazine with R₃e and R₃f; morpholine with R₃d and O; thiomorpholine with R₃d and S]

R₃ₐ, R₃ᵦ, R₃c, R₃d, R₃e and R₃f are independently selected from hydrogen, halogen, $C_{1-6}$ alkyl or $C_{1-6}$ haloalkyl; and R₄ is selected from $C_{1-6}$ alkyl, $C_{1-6}$ haloalkyl, $C_{3-7}$ cycloalkyl or 3- to 7-membered heterocyclyl.

7. The compound, or pharmaceutically acceptable salts, enantiomers, diastereomers, racemates, solvates, hydrates, polymorphs, or isotope variants thereof according to claim 5, wherein, R₃ is selected from

[structures: piperazine with R₃c; piperazine with R₃d and R₃e; piperazine with R₃e and R₃f; morpholine with R₃d and O; thiomorpholine with R₃d and S]

$R_{3a}$ and $R_{3b}$ are independently selected from hydrogen, halogen or $C_{1-6}$ alkyl;

$R_{3c}$, $R_{3d}$, $R_{3e}$ and $R_{3f}$ are independently selected from hydrogen or $C_{1-6}$ alkyl; and $R_4$ is $C_{1-6}$ alkyl or $C_{3-7}$ cycloalkyl.

8. The compound, or pharmaceutically acceptable salts, enantiomers, diastereomers, racemates, solvates, hydrates, polymorphs, or isotope variants thereof according to claim 5, wherein, $R_3$ is selected from

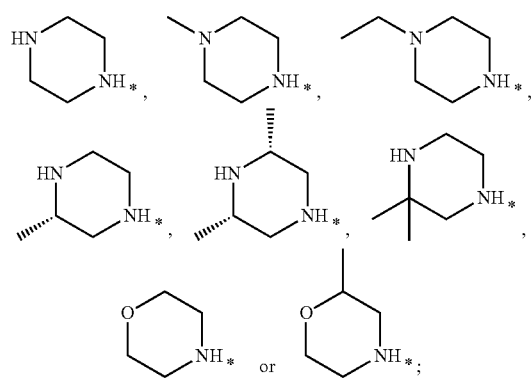

$R_{3a}$ and $R_{3b}$ are independently selected from hydrogen, halogen or $C_{1-6}$ alkyl; and $R_4$ is $C_{1-6}$ alkyl or $C_{3-7}$ cycloalkyl.

9. The compound, or pharmaceutically acceptable salts, enantiomers, diastereomers, racemates, solvates, hydrates, polymorphs, or isotope variants thereof according to claim 5, wherein, $R_3$ is selected from

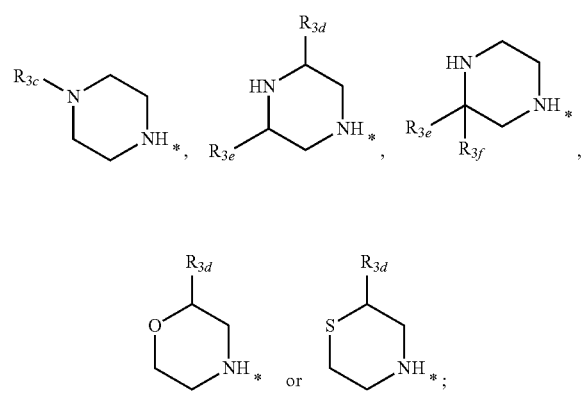

$R_{3a}$, $R_{3b}$, $R_{3c}$, $R_{3d}$, $R_{3e}$ and $R_{3f}$ are independently selected from hydrogen, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; and $R_4$ is selected from $C_{1-6}$ alkyl, $C_{1-6}$ haloalkyl, $C_{3-7}$ cycloalkyl or 3- to 7-membered heterocyclyl.

10. The compound, or pharmaceutically acceptable salts, enantiomers, diastereomers, racemates, solvates, hydrates, polymorphs, or isotope variants thereof according to claim 5, wherein, $R_3$ is selected from

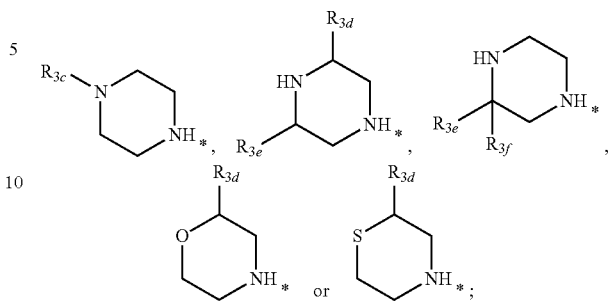

$R_{3a}$, $R_{3b}$, $R_{3c}$, $R_{3d}$, $R_{3e}$ and $R_{3f}$ are independently selected from hydrogen, $C_{1-6}$ alkyl or $C_{1-6}$ haloalkyl; and $R_4$ is selected from $C_{1-6}$ alkyl, $C_{1-6}$ haloalkyl, $C_{3-7}$ cycloalkyl or 3- to 7-membered heterocyclyl.

11. The compound, or pharmaceutically acceptable salts, enantiomers, diastereomers, racemates, solvates, hydrates, polymorphs, or isotope variants thereof according to claim 5, wherein, $R_3$ is selected from

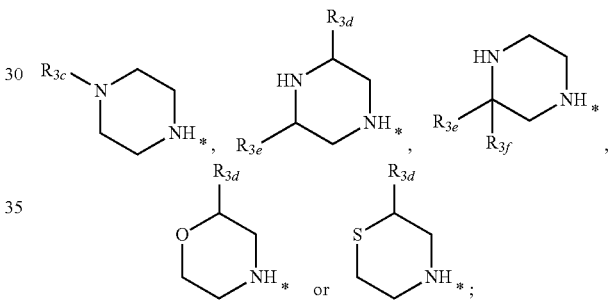

$R_{3a}$ and $R_{3b}$ are independently selected from hydrogen or $C_{1-6}$ alkyl;

$R_{3c}$, $R_{3d}$, $R_{3e}$ and $R_{3f}$ are independently selected from hydrogen or $C_{1-6}$ alkyl; and $R_4$ is $C_{1-6}$ alkyl or $C_{3-7}$ cycloalkyl.

12. The compound, or pharmaceutically acceptable salts, enantiomers, diastereomers, racemates, solvates, hydrates, polymorphs, or isotope variants thereof according to claim 5, wherein, $R_3$ is selected from

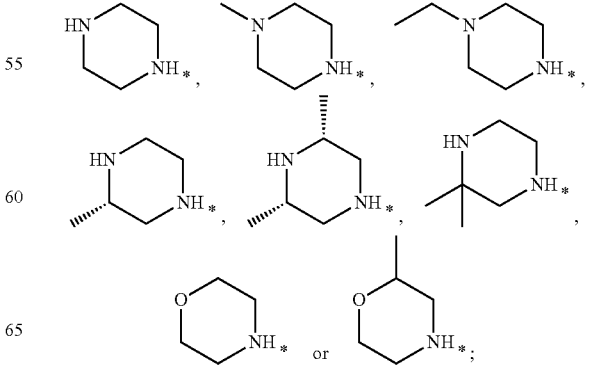

$R_{3a}$ and $R_{3b}$ are independently selected from hydrogen or $C_{1-6}$ alkyl; and
$R_4$ is $C_{1-6}$ alkyl or $C_{3-7}$ cycloalkyl.

13. The compound, or pharmaceutically acceptable salts, enantiomers, diastereomers, racemates, solvates, hydrates, polymorphs, or isotope variants thereof according to claim 5, wherein,
$R_3$ is

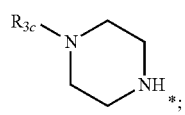

$R_{3a}$ and $R_{3b}$ are hydrogen;
$R_{3c}$ is $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; and
$R_4$ is $C_{1-6}$ alkyl or $C_{1-6}$ haloalkyl.

14. The compound, or pharmaceutically acceptable salts, enantiomers, diastereomers, racemates, solvates, hydrates, polymorphs, or isotope variants thereof according to claim 5, wherein,
$R_3$ is

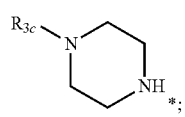

$R_{3a}$ and $R_{3b}$ are hydrogen;
$R_{3c}$ is $C_{1-6}$ alkyl or $C_{1-6}$ haloalkyl; and
$R_4$ is $C_{1-6}$ alkyl or $C_{1-6}$ haloalkyl.

15. The compound, or pharmaceutically acceptable salts, enantiomers, diastereomers, racemates, solvates, hydrates, polymorphs, or isotope variants thereof according to claim 5, wherein,
$R_3$ is

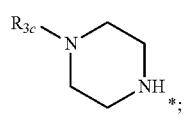

$R_{3a}$ and $R_{3b}$ are hydrogen;
$R_{3c}$ is $C_{1-6}$ alkyl; and
$R_4$ is $C_{1-6}$ alkyl.

16. The compound, or pharmaceutically acceptable salts, enantiomers, diastereomers, racemates, solvates, hydrates, polymorphs, or isotope variants thereof according to claim 1, wherein the compound is selected from:

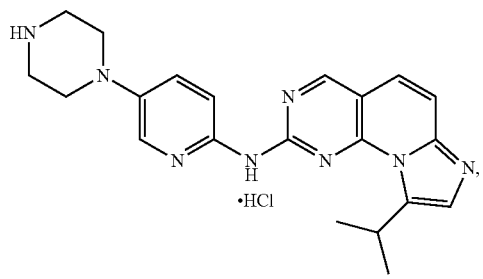

-continued

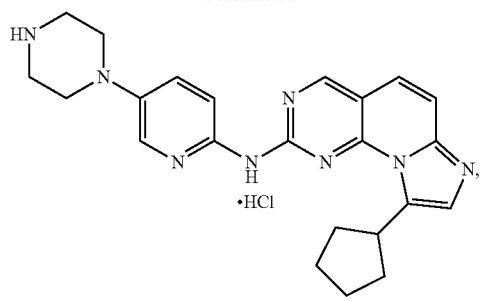

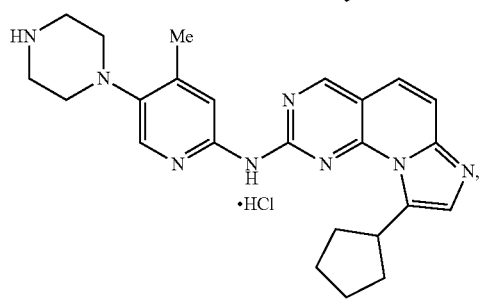

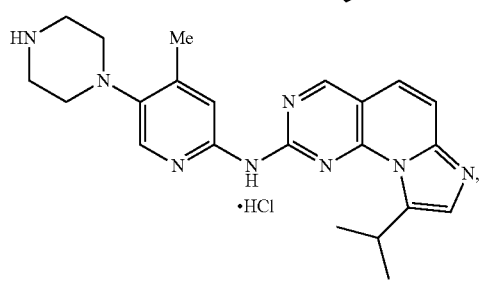

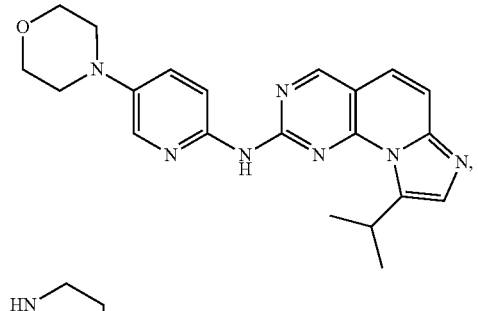

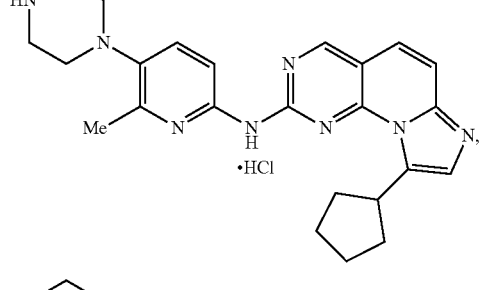

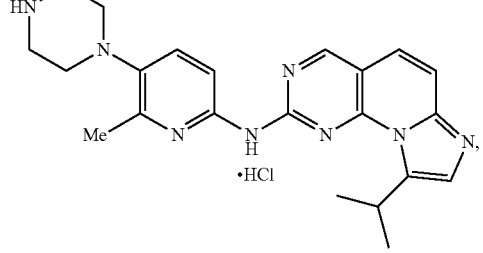

75
-continued
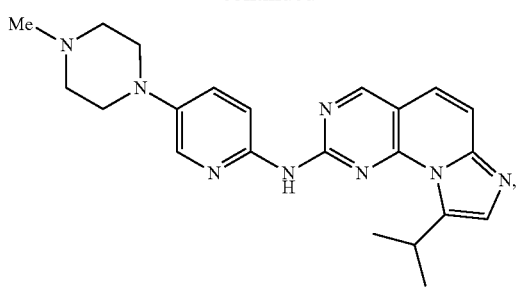
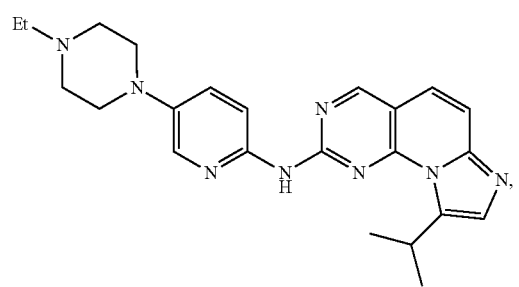
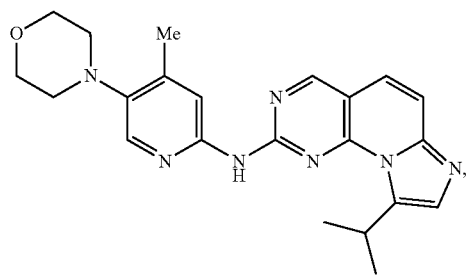
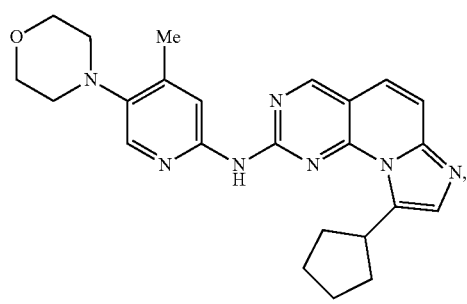
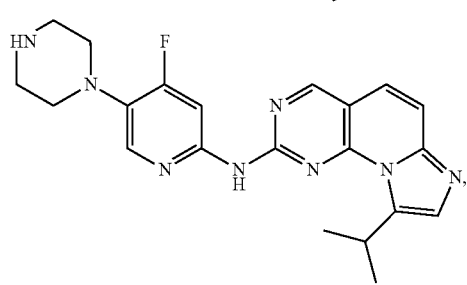
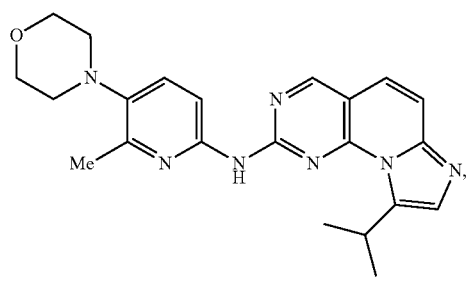
76
-continued
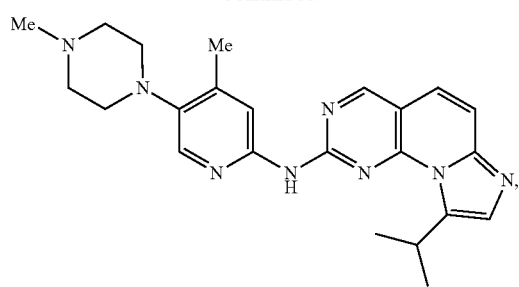
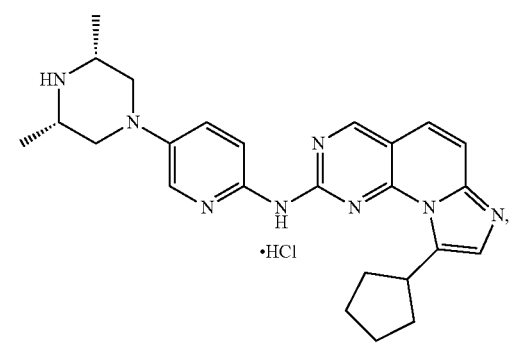
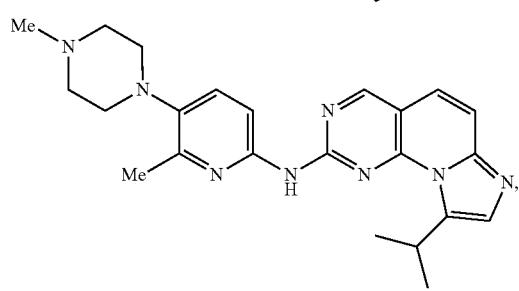
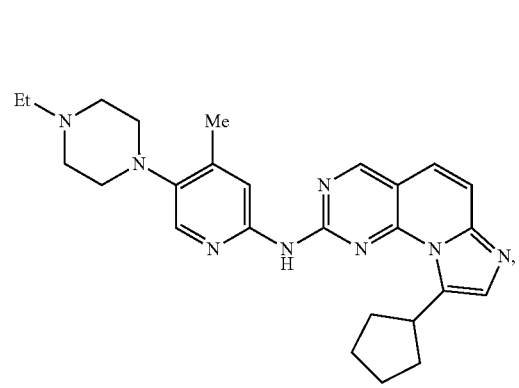
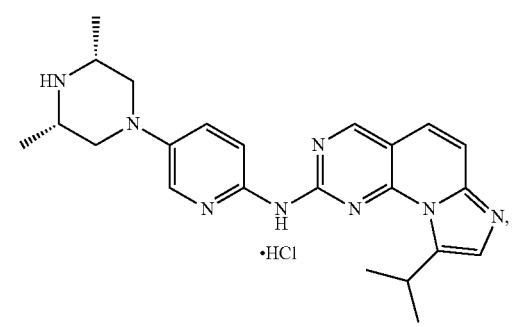

77
-continued
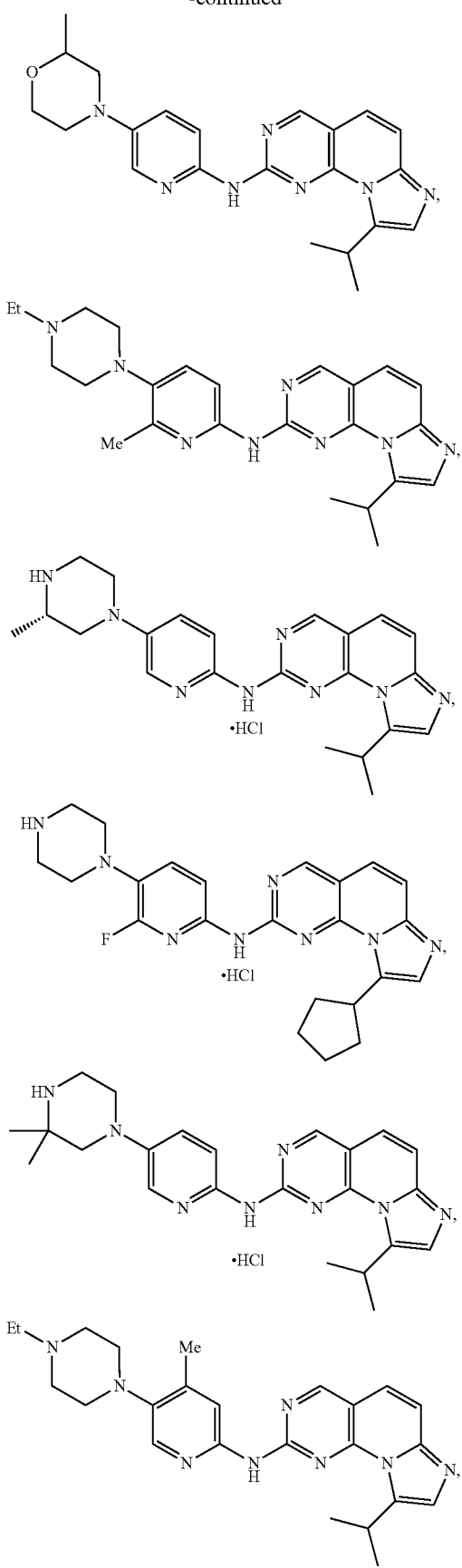
78
-continued
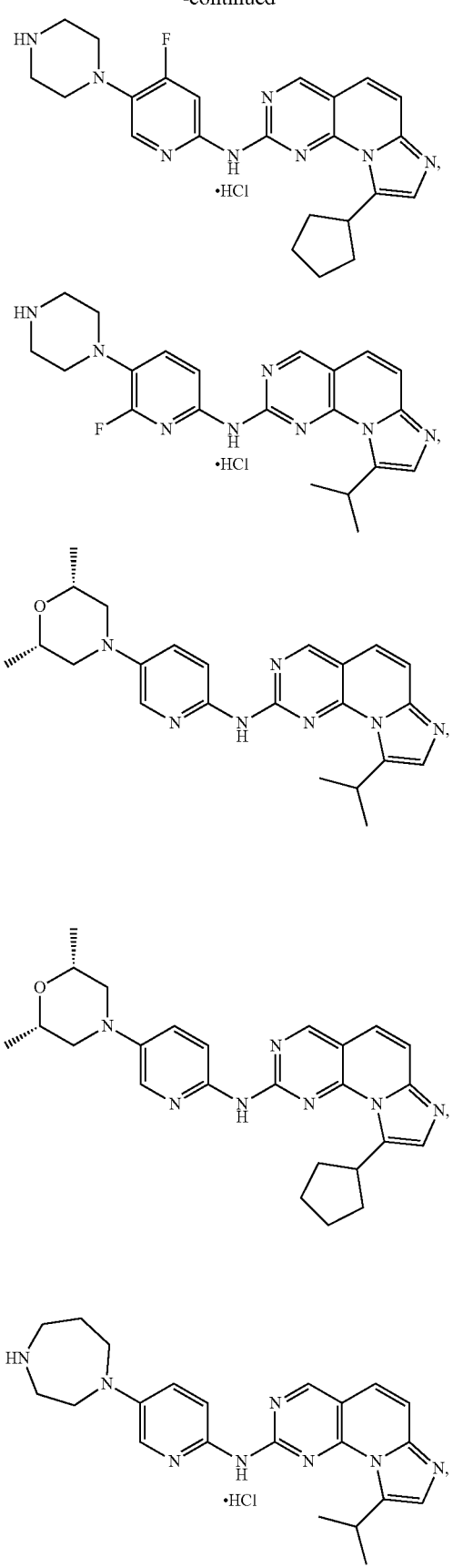

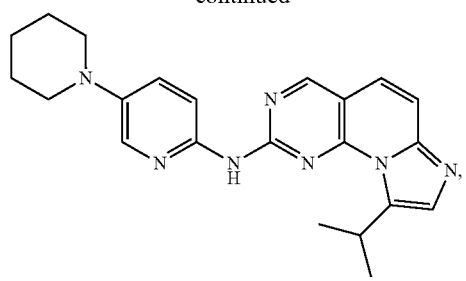
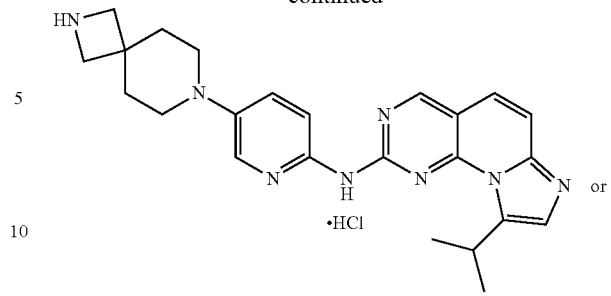 or
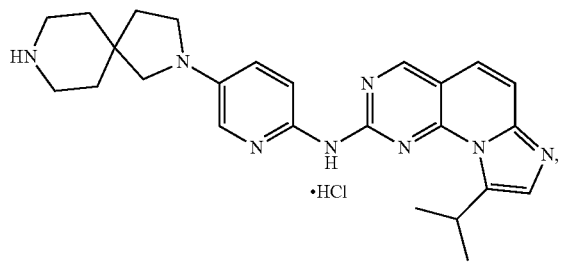
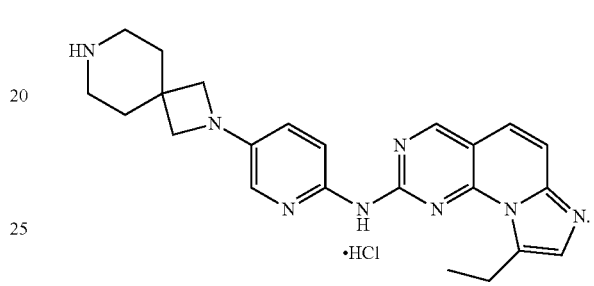
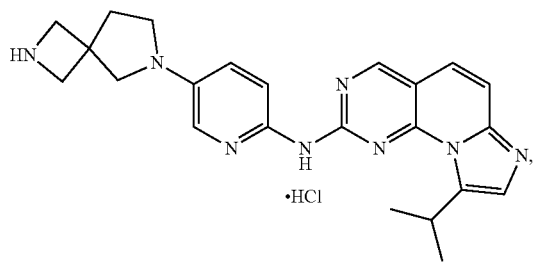
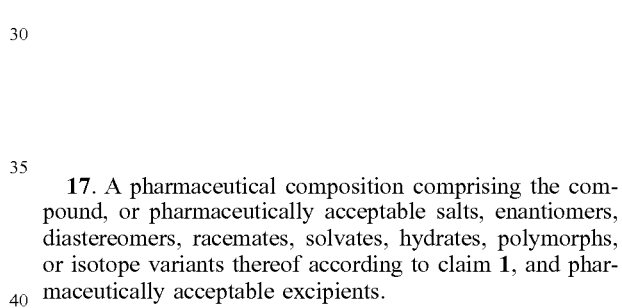
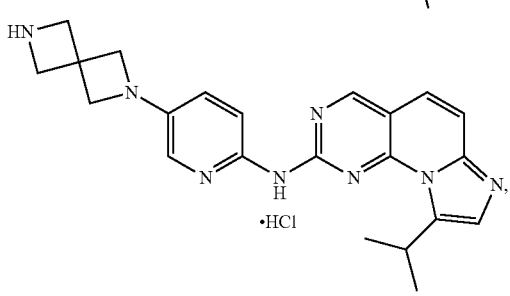
17. A pharmaceutical composition comprising the compound, or pharmaceutically acceptable salts, enantiomers, diastereomers, racemates, solvates, hydrates, polymorphs, or isotope variants thereof according to claim 1, and pharmaceutically acceptable excipients.
18. The pharmaceutical composition of claim 17, which further comprises other therapeutic agents.
* * * * *

UNITED STATES PATENT AND TRADEMARK OFFICE
CERTIFICATE OF CORRECTION

PATENT NO. : 11,091,485 B2
APPLICATION NO. : 16/619222
DATED : August 17, 2021
INVENTOR(S) : Bin Liu et al.

Page 1 of 1

It is certified that error appears in the above-identified patent and that said Letters Patent is hereby corrected as shown below:

In the Claims

In Claim 16, at Column 75, Lines 45-55, please replace the formula:

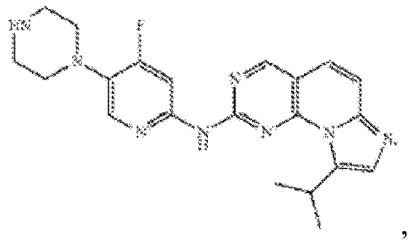
,

With the formula below:

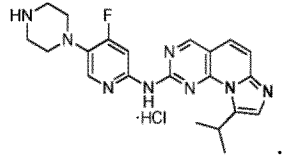
.

In Claim 16, at Column 80, Lines 15-30, please replace the formula:

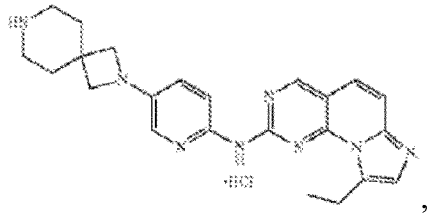
,

With the formula below:

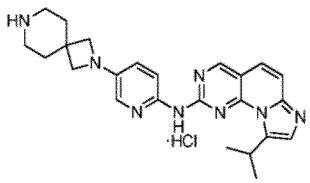
.

Signed and Sealed this
Third Day of September, 2024

Katherine Kelly Vidal
Director of the United States Patent and Trademark Office